US007233818B1

(12) United States Patent
Aletras et al.

(10) Patent No.: US 7,233,818 B1
(45) Date of Patent: Jun. 19, 2007

(54) METHODS AND APPARATUS FOR MAPPING INTERNAL AND BULK MOTION OF AN OBJECT WITH PHASE LABELING IN MAGNETIC RESONANCE IMAGING

(75) Inventors: Anthony H. Aletras, Rockville, MD (US); Han Wen, Bethesda, MD (US)

(73) Assignee: United States of America as represented by the Secretary of the Department of Health and Human Services, Washington, DC (US)

( * ) Notice: Subject to any disclaimer, the term of this patent is extended or adjusted under 35 U.S.C. 154(b) by 706 days.

(21) Appl. No.: 10/049,005

(22) PCT Filed: Aug. 4, 2000

(86) PCT No.: PCT/US00/21299

§ 371 (c)(1),
(2), (4) Date: Mar. 1, 2002

(87) PCT Pub. No.: WO01/11380

PCT Pub. Date: Feb. 15, 2001

Related U.S. Application Data

(60) Provisional application No. 60/201,056, filed on May 1, 2000, provisional application No. 60/165,564, filed on Nov. 15, 1999, provisional application No. 60/147,314, filed on Aug. 5, 1999.

(51) Int. Cl.
*A61B 5/055* (2006.01)
(52) U.S. Cl. .................... 600/410; 324/307; 324/309

(58) Field of Classification Search ............ 600/410, 600/419; 324/306–309
See application file for complete search history.

(56) References Cited

U.S. PATENT DOCUMENTS

| 4,484,138 A | 11/1984 | Bottomley et al. |
| 4,707,658 A | 11/1987 | Frahm et al. |
| 4,797,615 A | 1/1989 | Rotem et al. |
| 4,891,595 A | 1/1990 | Granot |

(Continued)

FOREIGN PATENT DOCUMENTS

EP 93302025.7 3/1993

OTHER PUBLICATIONS

Pauly, et al. "A k-Space Analysis of Small-Tip-Angle Excitation," *Journal of Magnetic Resonance*, vol. 81, pp. 43-56 (1989).

(Continued)

*Primary Examiner*—Ruth S. Smith
(74) *Attorney, Agent, or Firm*—Klarquist Sparkman, LLP

(57) ABSTRACT

Magnetic resonance imaging method and apparatus are provided for mapping the internal or bulk motion of an object by labeling the phase of a specimen magnetization with a selected spatial function and measuring changes in the phase of the magnetization. The spatial function is selectable to provide magnetization phase modulation corresponding to displacements in a selected direction, such as a radial or azimuthal direction. Methods and apparatus for producing images based on magnetization phase modulation acquire image data based on stimulated echos and stimulated anti-echos. In an embodiment, a series of 180 degree pulses produces alternating stimulated and stimulated anti-echos that are measured and assigned to respective images.

30 Claims, 9 Drawing Sheets

U.S. PATENT DOCUMENTS

| | | | |
|---|---|---|---|
| 5,379,766 A | 1/1995 | McKinnon et al. | |
| 5,429,134 A | 7/1995 | Foo | |
| 5,492,123 A | 2/1996 | Edelman | |
| 5,701,074 A * | 12/1997 | Zhu | 324/307 |
| 6,076,006 A | 6/2000 | Van Den Brink et al. | |
| 6,703,835 B2 * | 3/2004 | Patch et al. | 324/307 |

OTHER PUBLICATIONS

Frahm, et al. "High-Speed STEAM MRI of the Human Heart," *Magnetic Resonance in Medicine*, vol. 22, pp. 133-142 (1991).

Norris, et al. "On the Application of Ultra-fast RARE Experiments," *Magnetic Resonance in Medicine*, vol. 27, pp. 142-164 (1992).

Fischer, et al. "Limitations of Stimulated Echo Acquisition Mode (STEAM) Techniques in Cardiac Applications," *MRM*, vol. 34, pp. 80-91 (1995).

Reese, et al. "Measuring Diffusion in the Presence of Material Strain," Journal of Magnetic Resonance, vol. 112, pp. 253-258 (1996).

Morgan, et al. "Application of linear optimization techniques to MRI phase contrast bloof flow measurements," *Magnetic Resonance Imaging*, vol. 14(9), pp. 1043-1051 (1996) (Abstract).

Alsop "The Sensitivity of Low Flip Angle RARE Imaging," *MRM*, vol. 37, pp. 176-184 (1997).

Schick "SPLICE: Sub-Second Diffusion-Sensitive MR Imaging Using a Modified Fast Spin-Echo Aquisition Mode," *MRM*, vol. 38, pp. 638-644 (1997).

Chenevert, et al. "Elasticity Reconstructive Imaging by Means of Stimulated Echo MRI," *MRM*, vol. 39, pp. 482-490 (1998).

Aletras, et al. "High-Resolution Strain Analysis of the Human Heart with Fast-DENSE," *Journal of Magnetic Resonance*, vol. 140, pp. 41-57 (1999).

Aletras, et al. "DENSE: Displacement Encoding with Stimulated Echoes in Cardiac Functional MRI," *Journal of Magnetic Resonance*, vol. 137, pp. 247-252 (1999).

Zhu, et al. "Stimulated Anti-Echo Selection in Spatially Localized NMR Spectroscopy," Journal of Magentic Resonance, vol. 136, pp. 1-5 (1999).

Aletras, et al. "High Resolution Strain Analysis of the Human Heart with Fast-DENSE," *Proc. Intl. Soc. Magn. Reson. Med.*, vol. 7, pp. 1286 (1999).

Kerwin, et al. "A k-Space Analysis of MR Tagging," *Journal of Magnetic Resonance*, vol. 142, pp. 313-322 (2000).

Garot, et al. "Fast determination of regional myocardial strain fields from tagged cardiac images using harmonic phase MRI," *Circulation*, vol. 101(9) pp. 981-988 (2000) (Abstract).

Mulkern, et al. "From signal to image: magnetic resonance imaging physics for cardiac magnetic resonance," *Pediactric Cardiology*, vol. 21(1) pp. 5-17 (2000) (Abstract).

Chung "Assessment of cardiovascular anatomy in patients with congenital heart disease by magnetic resonance imaging," *Pediatric Cardiology*, vol. 21(1) pp. 18-26 (2000) (Abstract).

Huang, et al. "Spatio-temporal tracking of myocardial deformations with a 4-D B-spline model from tagged MRI," *IEEE Transations on Medical Imaging*, vol. 18(10) pp. 957-972 (1999) (Abstract).

Lim, et al. "MRI of myocardial infarction," *Journal of Magnetic Resonance Imaging*, vol. 10(5) pp. 686-693 (1999) (Abstract).

Wilke, et al. "Magnetic resonance first-pass myocardial perfusion imaging: clinical validation and future applications," *Journal of Magnetic Resonance Imaging*, vol. 10(5) pp. 676-685 (1999) (Abstract).

Sechtem, et al. "Stress functional MRI: detection of ischemic heart disease and myocardial viability," *Journal of Magnetic Resonance Imaging*, vol. 10(5) pp. 667-675 (1999) (Abstract).

Schwitter, et al. "Assessment of myocardial function and perfusion in a canine model of non-occlusive coronary artery stenosis using fast magnetic resonance imaging," *Journal of Magnetic Resonance Imaging*, vol. 9(1) pp. 101-110 (1999) (Abstract).

Stuber, et al. "Quantification of the local heartwall motion by magnetic resonance myocardial tagging," *Computerized Medical Imaging & Graphics*, vol. 22(3) pp. 217-228 (1998) (Abstract).

Reddy, et al. "Congenital heart disease: measuring physiology with MRI," *Seminars in Roentgenology*, vol. 33(3) pp. 228-238 (1998) (Abstract).

Hennig, et al. "Analysis of myocardial motion based on velocity measurements with a black blood prepared segmented gradient-echo sequence: methodology and applications to normal volunteers and patients," *Journal of Magnetic Resonance Imaging*, vol. 8(4) pp. 868-877 (1998) (Abstract).

Slawson, et al. "Cardiac MRI of the normal and hypertrophied mouse heart," *Magnetic Resonance in Medicine*, vol. 39(6) pp. 980-987 (1998) (Abstract).

Friedrich, et al. "Contrast media-enhanced magnetic resonance imaging visualizes myocardial changes in the course of viral myocarditis," *Circulation*, vol. 97(18) pp. 1802-1809 (1998) (Abstract).

Feinstein, et al. "Using cardiac phase to order reconstruction (CAPTOR): a method to improve diastolic images," *Journal of Magnetic Resonance Imaging*, vol. 7(5) pp. 794-798 (1997) (Abstract).

Frayne, et al. "Effect of and correction for in-plane myocardial motion on estimates of coronary-volume flow rates," *Journal of Magnetic Resonance Imaging*, vol. 7(5) pp. 815-828 (1997) (Abstract).

Jivan, et al. "Dynamic T1 measurement using snapshot-FLASH MRI," *Journal of Magnetic Resonance*, vol. 127(1) pp. 65-72 (1997) (Abstract).

Siri, et al. "Gated magnetic resonance imaging of normal and hypertrophied murine hearts," *American Journal of Physiology*, vol. 272 p. 2394-2402 (1997) (Abstract).

Robson, et al. "Three-dimensional strain-rate imaging," *Magnetic Resonance in Medicine*, vol. 36(4) pp. 537-546 (1996) (Abstract).

Riederer, "The future technical development of MRI," *Journal of Magnetic Resonance Imaging*, vol. 6(1) pp. 52-56 (1996) (Abstract).

Fischer et al., "Improved Myocardial Tagging Contrast," Inst. Biomedical Engineering and Medical Informatics pp. 191-200 (1993).

Kuijer et al., "Improved Harmonic Phase Myocardial Strain Maps," Mag. Res. Med. 46:993-999 (2001).

Callot et al., "In Vivo Study of Microcirculation in Canine Myocardium Using the IVIM Method," Mag. Res. in Med. 50:531-540 (2003).

* cited by examiner

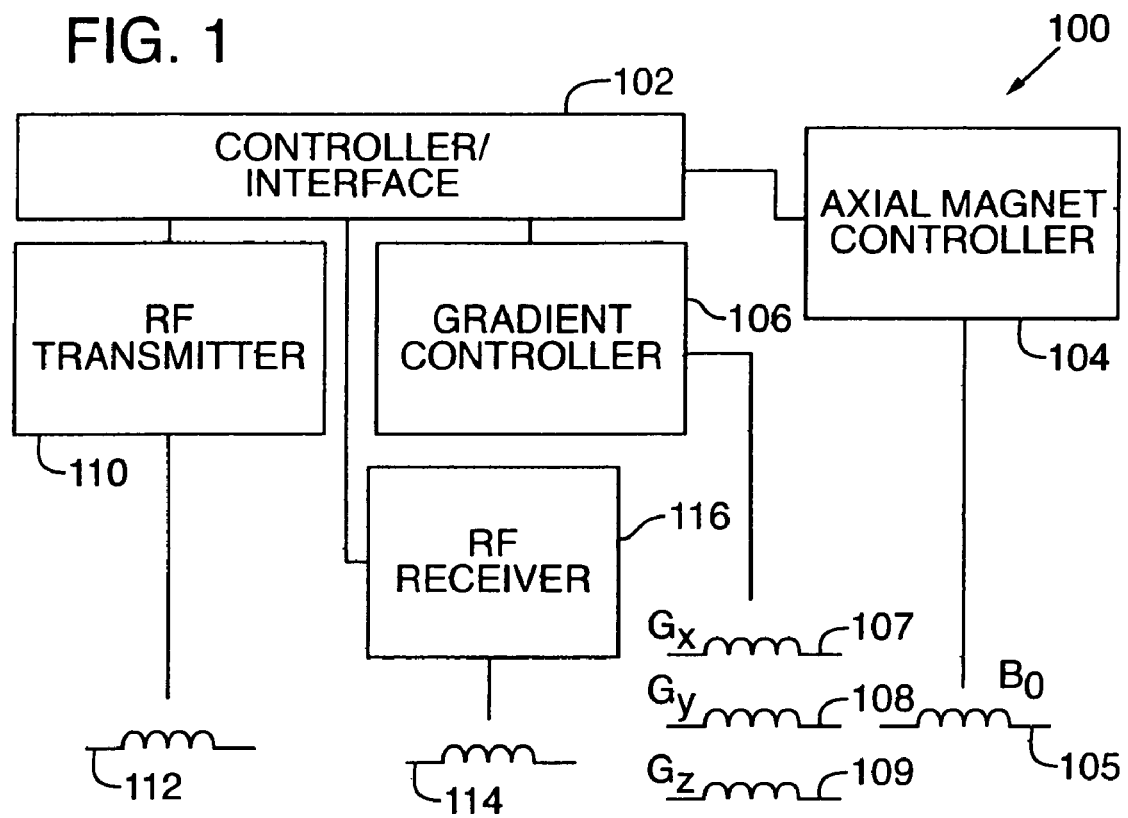

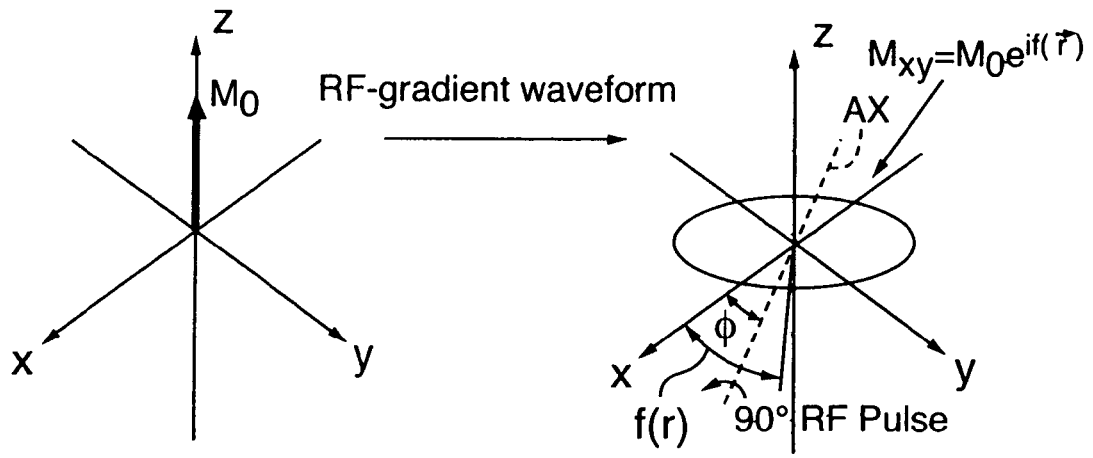
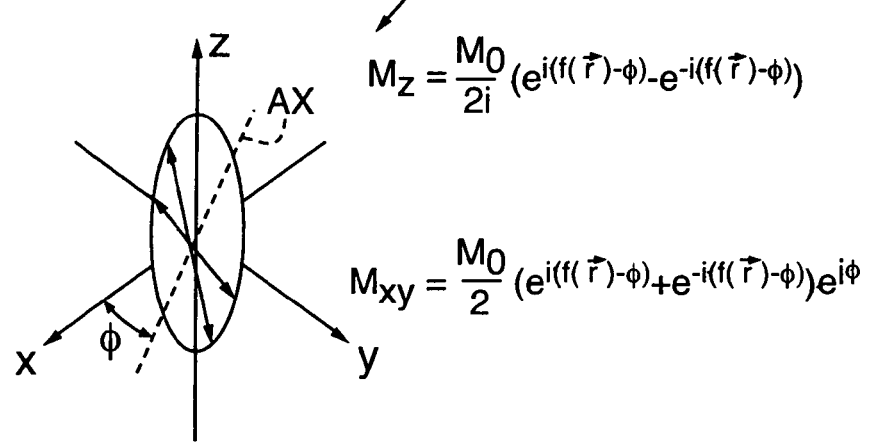
FIG. 4A
FIG. 4B
FIG. 4C

FIG. 11A
$M_{xy}=M_0 e^{if(\vec{r})}$
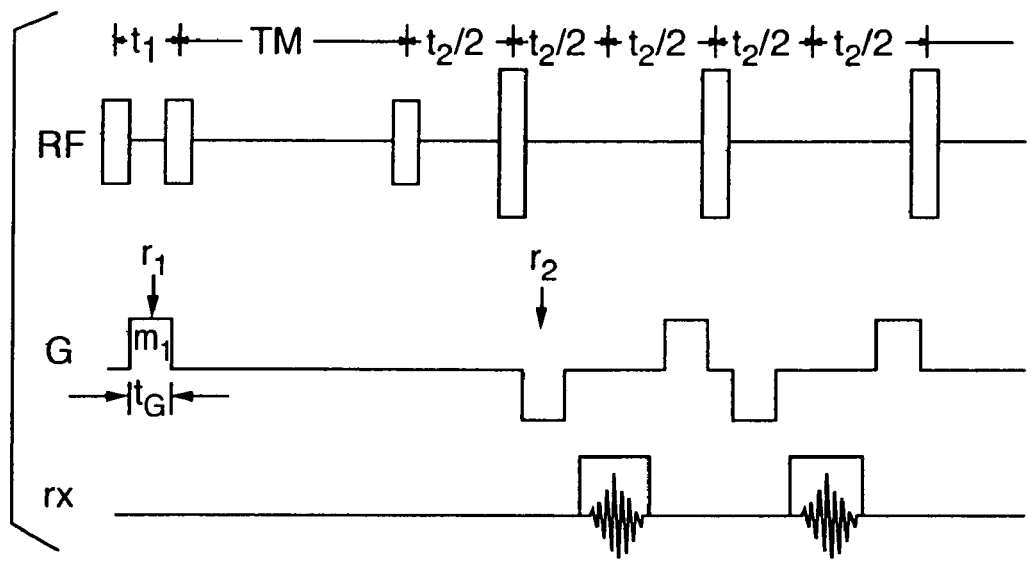
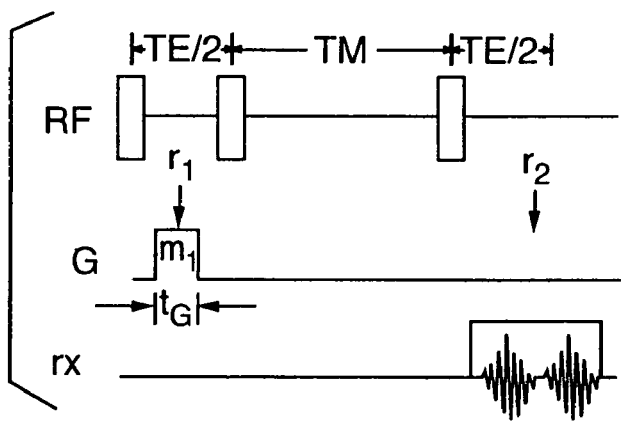
FIG. 11B
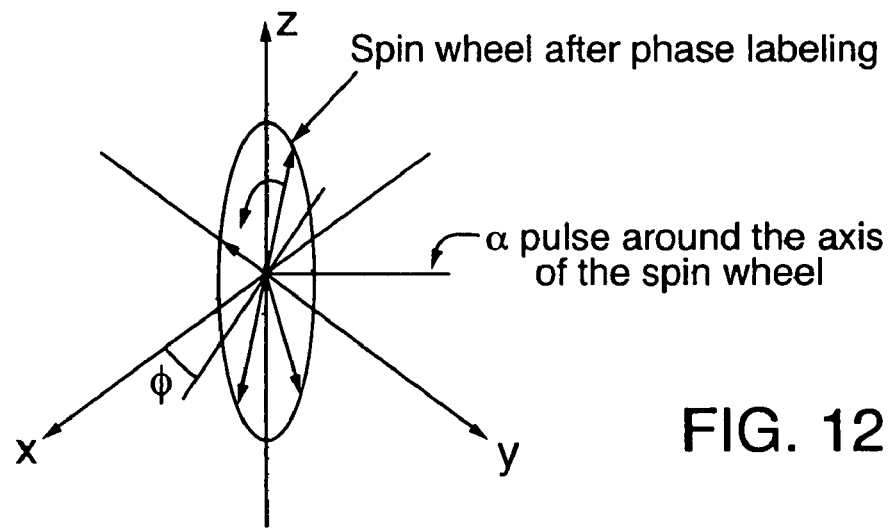
FIG. 12

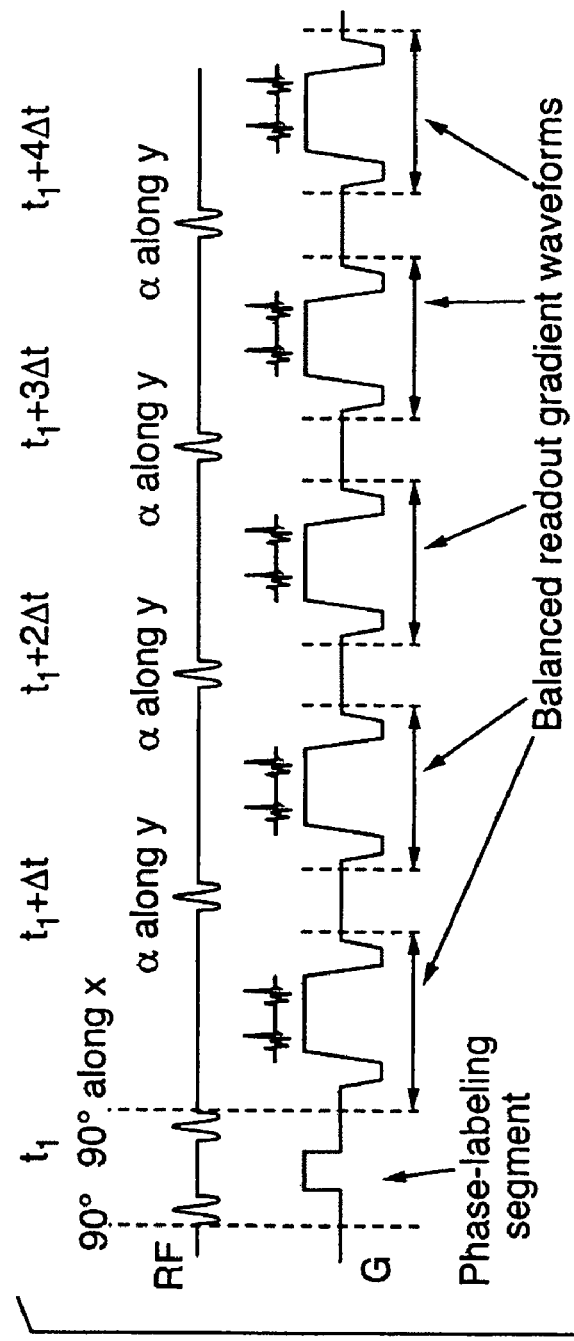
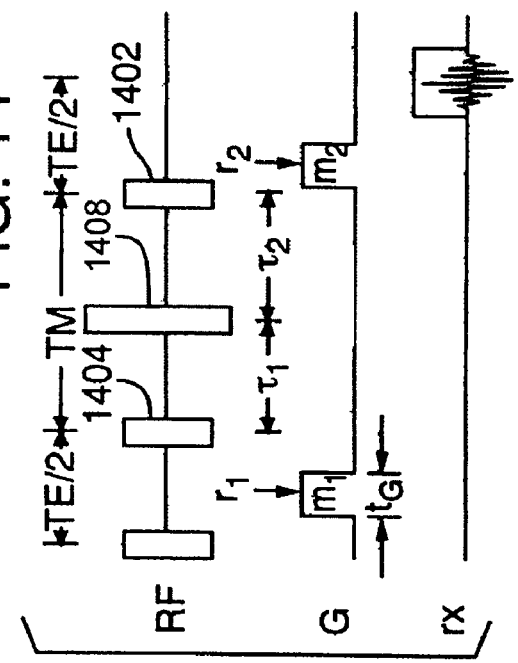
FIG. 13
FIG. 14

METHODS AND APPARATUS FOR MAPPING INTERNAL AND BULK MOTION OF AN OBJECT WITH PHASE LABELING IN MAGNETIC RESONANCE IMAGING

PRIORITY CLAIM

This is a § 371 U.S. national stage of PCT/US00/21299, filed Aug. 4, 2000, which was published in English under PCT Article 21(2), and claims the benefit of U.S. application Ser. No. 60/147,314, filed Aug. 5, 1999, U.S. application Ser. No. 60/165,564, filed Nov. 15, 1999, and U.S. application Ser. No. 60/201,056, filed May 1, 2000.

FIELD OF THE INVENTION

The invention pertains to methods and apparatus for magnetic resonance imaging.

BACKGROUND

Magnetic resonance imaging ("MRI") is a noninvasive imaging method widely used for medical diagnostics. To date, MRI methods for tracking the motion of an object over relatively long periods of time have been based on spatially modulating magnitude of the specimen magnetization according to a specific grid pattern, and observing the deformation of this grid pattern as motion occurs. In order to quantify the displacement vector of any small volume element (voxel), the positions of the grid lines and their intersection points are precisely defined. This usually requires human assistance, and precision is limited by image resolution or voxel size. The motion of voxels between grid lines cannot be measured directly, and interpolation methods are used to estimate motion.

Other MRI methods measure voxel velocity by subjecting the transverse magnetization to a biphasic gradient pulse before readout, so that stationary spins do not accumulate a net phase change, while spins with nonzero velocity components along the gradient direction accumulate a phase change. By measuring such phase changes, one or more velocity components can be derived. While phase-contrast velocity mapping generally provides high spatial resolution and simple data processing, it is generally unsuitable for motion tracking, as it requires integration of velocity vectors from multiple measurements and mathematically tracking voxel positions. These integrations and voxel position tracking are difficult and prone to error.

SUMMARY

Internal and bulk motion of a specimen are mapped by labeling the phase of the specimen magnetization with a selected function of position at an initial time and measuring changes in the phase of the magnetization. Either or both of a longitudinal and a transverse component of specimen magnetization can be phase labeled based on the selected function. A phase labeled component of magnetization is stored by rotating the component to align with a longitudinal axis that is defined by an applied magnetic field. The time varying phase of the specimen magnetization is measured by producing stimulated echos or stimulated anti-echos, or both from the phase labeled magnetization. Measurements of the stimulated echos and the stimulated anti-echos are processed to produce respective images. The phase labeling function can provide a phase modulation based on displacement along any direction. For example, the selected function can be as a function of an azimuthal or other angle, so that rotational displacements produce phase shifts in the specimen magnetization.

These and other features and advantages are described below with reference to the accompanying drawings.

BRIEF DESCRIPTION OF THE DRAWINGS

FIG. 1 is a schematic block diagram of a magnetic resonance (MR) imaging system.

FIGS. 4A-4C illustrate phase labeling of a longitudinal and transverse magnetization based on a function f(r).

FIG. 11A illustrates RF and gradient pulses applied to an image of a phase labeled specimen in an alternating dual echo imaging method.

FIG. 11B illustrates RF and gradient pulses applied to an image of a phase labeled specimen in a simultaneous dual echo imaging method.

FIG. 12 illustrates a magnetization spin wheel.

FIG. 13 is a diagram of a sequence of RF and gradient pulses applied according to an embodiment of a rotating wheel method of acquiring phase labeled data.

FIG. 14 illustrates RF and gradient pulses of a dual-echo method configured to reduce free induction decay.

DETAILED DESCRIPTION

Figure 2A:
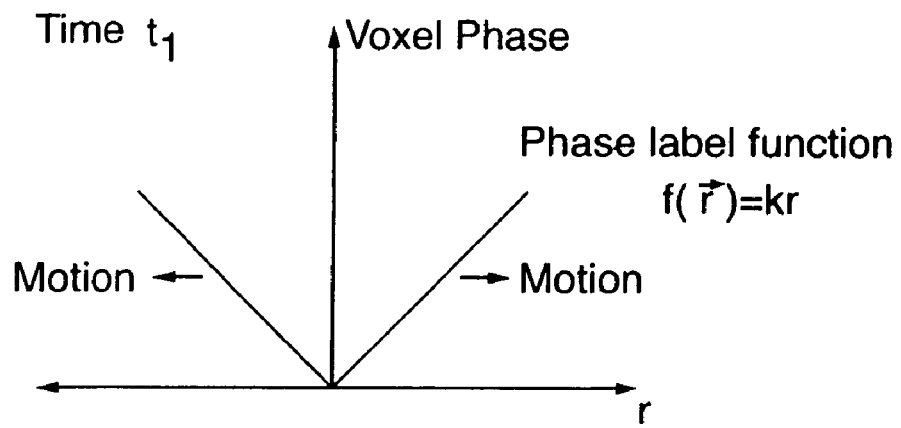
FIGS. 2A-2B illustrate volume element ("voxel") phase labeling based on a function f(r).

FIG. 1 is a schematic block diagram of a magnetic resonance imaging (MRI) system 100 that provides images of a specimen. The MRI system 100 includes a controller 102 that is typically programmed by a clinician with a series of commands corresponding to a particular imaging sequence. The command sequences can be entered with a keyboard, a pointing device such as a mouse, or other input device. Command sequences can be stored by the controller 102 for retrieval from a hard disk, floppy disk, or other computer readable media and can be selected from a menu, so that a clinician can easily select among an imaging protocol from various command sequences.

The MRI system 100 includes an axial magnet controller 104 that controls the spatial homogeneity of an axial magnetic field $B_0$ with an axial field coil 105. As used herein, the axial magnetic field $B_0$ is directed along a +z-axis in a xyz coordinate system. A plane parallel to an xy-plane (perpendicular to the z-axis) is referred to as a transverse plane. A gradient controller 106 activates gradient coils 107-109 that produce a magnetic field gradients $G_x$, $G_y$, $G_z$. For convenience, the magnetic field gradients $G_x$, $G_y$, $G_z$ are represented generically as G. The magnetic field gradients are typically applied as pulses.

A radio-frequency (RF) transmitter 110 is configured to generate RF pulses that are applied to a transmitter coil 112 to produce a pulsed magnetic field. A receiver coil 114 detects changes in magnetization in the specimen and communicates the detected magnetization changes to an RF receiver 116. The RF receiver 116 processes the detected magnetization changes and provides image data to the controller 102 based on these changes.

A specimen to be imaged is exposed to the axial magnetic field $B_0$ and a field gradient G selected by the controller 102. An RF pulse is applied to produce a change in magnetization that is detected by the receiver coil 114 and processed by the RF receiver 116. The RF pulse is typically represented as product of a pulse envelope $B_1$ and a complex exponential $\exp(i\omega_{RF}t)$, wherein t is time, i is the square root of −1, and $\omega_{RF}$ is an excitation carrier frequency. The excitation frequency $\omega_{RF}$ is generally selected to be approximately equal to a resonance frequency of one or more constituents of the specimen. The resonance frequency $\omega_0$ is proportional to a product of a gyromagnetic ratio $\gamma$ (a material constant) and a magnitude of the axial field $B_0$. By applying a field gradient G with the gradient coils 107-109 so that the specimen is exposed to a non-uniform magnetic field, slices of the specimen can be selected for imaging. Within a selected slice, the resonance frequency $\omega_{RF}$ is sufficiently constant so that the RF receiver 116 can reject magnetization changes in non-selected slices by rejecting frequency components corresponding to the non-selected slices. Detecting changes in magnetization slice by slice permits image formation.

With only the axial magnetic field $B_0$ applied, some magnetic dipoles of sample constituents align with the axial magnetic field $B_0$ to produce an equilibrium magnetization $M_0$ that generally has only a +z-directed component. The specimen include individual magnetic dipoles of dipole moment $\mu$ that precess about the direction of $B_0$ (the z-axis) at the frequency $\omega_0 = \gamma B_0$ that is also referred to as the Larmor frequency. Changes in magnetization are generally described with reference to an xyz coordinate system that rotates about the axial direction at the Larmor frequency. The z-axis of such a rotating coordinate system is the same as the z-axis of a stationary coordinate system while the x-axis of the rotating coordinate system rotate in a transverse plane.

Application of a selected RF pulse can rotate a magnetization or one or more components thereof. An RF pulse of duration and magnitude sufficient to produce a 180 degree rotation is referred to as a 180 degree pulse and an RF pulse sufficient to produce a 90 degree rotation is referred to as a 90 degree pulse. In general, an RF pulse sufficient to produce a rotation $\alpha$ is referred to as an $\alpha$ pulse. The axis of rotation of such pulses can be selected based on the direction in which the corresponding pulse magnetic field is applied.

Vector quantities are expressed herein in boldface. A transverse component $M_{xy}$ of a (vector) magnetization M (i.e., a component of the magnetization M in the xy-plane) is expressed as $Me^{i\theta}$, wherein an x-component is a real part of $Me^{i\theta}$, a y-component is an imaginary part of $Me^{i\theta}$, and M is a magnitude of the magnetization M.

Phase Labeling

In some specimens, some volume elements ("voxels") are moving and experience a displacement between an initial time $t_1$ and a subsequent time $t_2$. For example, a portion of a specimen moving parallel to the x-axis acquires an x-directed displacement. The magnetization M can be encoded (i.e., modulated) based upon such displacements. Such a modulation can be a function of position and can be generally expressed as $f(r(t_2))-f(r(t_1))$, wherein $r(t_2)$ and $r(t_1)$ are positions of a voxel at times $t_2$ and $t_1$, respectively, and f(r) is an arbitrary function of position r. Modulation of the magnetization based on displacements permits imaging based upon displacement.

The magnetization can be amplitude modulated, frequency modulated, or phase modulated. Phase modulation can be accomplished by modulating the magnetization M or a component of the magnetization M with a phase factor $e^{if(r)}$ at a time $t_1$, producing a phase modulated magnetization. A phase factor such as $e^{if(r)}$ is referred to herein as a "phase label." The phase modulated magnetization can be preserved until a time $t_2$, when an MR image is acquired based on the phase modulation. A voxel that is displaced to a position $r(t_2)$ retains a phase factor based on $f(r(t_1))$ and can be further modulated or demodulated with a phase factor based on $f(r(t_2))$ to produce an image based on $f(r(t_2))-f(r(t_1))$. RF and gradient pulses that provide a selected modulation or phase labeling can be selected to provide phase modulation according to a function f(r).

Figure 2B:
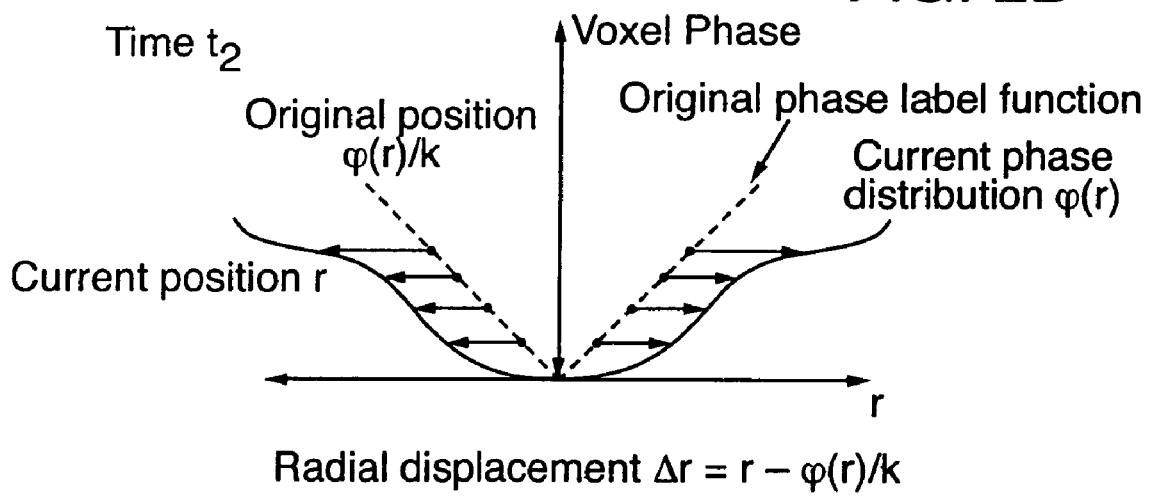

FIGS. 2A-2B illustrate phase labeling based on a function f(r)=kr, wherein r is a radial coordinate in a cylindrical (r, $\theta$, z) coordinate system and k is a constant. A corresponding phase label is $e^{ikr}$. With such a phase label, a voxel acquires a phase proportional to a change in radial coordinate between times $t_1$ and $t_2$, i.e., a change in distance between the voxel and an origin of the cylindrical coordinate system. At time $t_1$, a phase proportional to kr is applied so that voxel phase as a function of the radial coordinate is f(r)=kr with a corresponding phase label $e^{ikr}$. At time $t_2$, voxels are displaced from voxel positions at time $t_1$ and the voxel phase label is $e^{i\Phi(r)}$. The phase $\Phi(r)$ is produced by a combination of the initial phase labeling with $e^{ikr}$ and changes in the phase as a function of position produced by displacements. A radial displacement $\Delta r$ of a voxel can be obtained from a measurement of the phase $\Phi(r)$ as $\Delta r = r - \Phi(r)/k$ and a radial coordinate of a voxel at time $t_2$ is $\Phi(r)/k$.

In a Cartesian (x,y,z) coordinate system, the magnetization M includes a longitudinal component $M_z$ and a transverse component $M_{xy}$ and can be phase labeled in several ways. The longitudinal component $M_z$ can be phase labeled using RF and gradient pulses to apply a modulation $m(r)e^{if(r)}$, wherein m(r) is a real function of position r, and f(r) is a phase-labeling function. Because the longitudinal magnetization $M_z$ is a scalar, and therefore a real number, the longitudinal magnetization $M_z$ also contains a complex conjugate term $m(r)e^{if(r)}$. Alternatively, the transverse component $M_{xy}$ can be labeled with a combination of RF and gradient pulses to include modulations corresponding to $m(r)e^{if(r)}$, $m(r)e^{if(r)}$, or a combination of both. In addition, both the longitudinal and transverse components can be labeled to include phase-labeled terms such as $e^{if(r)}$, $e^{-if(r)}$, or both.

To produce a transverse magnetization having a selected phase modulation according to a function f(r), the equilibrium magnetization $M_0$ is typically rotated into the transverse plane with a combination of RF and gradient pulses. Such a pulse combination can be determined based on the following equations for rates of change of $M_{xy}$ and $M_z$ found in, for example, Pauly et al., J. Magn. Resonan. 81:43-56 (1989):

$$\dot{M}_{xy} = i\gamma G \cdot r M_{xy} + i\gamma B_1 M_z,$$

$$\dot{M}_z = -\gamma \langle M_{xy} \cdot B_1 \rangle,$$

where G represents an applied magnetic field gradient and $B_1$ is an amplitude of the RF pulse. By integrating these equations, $M_{xy}$ can be determined as a function of position r and time t:

$$M_{xy}(r, t) = i\gamma M_0 \int_0^t B_1(\tau) e^{ir\cdot k(\tau)} d\tau + i\gamma^2 \int_0^t d\tau B_1(\tau) e^{ir\cdot k(\tau)} \int_0^\tau \langle M_{xy}(r, s) \cdot iB_1(s) \rangle ds,$$

wherein k(t) is a k-space trajectory driven by the gradient G as defined in Pauly et al. If the RF-gradient pulse combination is to produce $M_{xy}(r,T) = m(r)e^{if(r)}$ at a time T corresponding to the conclusion of the RF-gradient pulse combination, then the RF pulse can be selected so that $$\int_0^t B_1(t) e^{ir\cdot k(t)} dt =$$

$$-\frac{i}{\gamma M_0} M_{xy}(r, T) - \frac{\gamma}{M_0} \int_0^T d\tau B_1(\tau) e^{ir\cdot k(\tau)} \int_0^\tau \langle M_{xy}(r, s) \cdot iB_1(s) \rangle ds.$$

If m(r) is small compared to the magnetization $M_0$, the small-tip-angle approximation of Pauly et al. can be used and $B_1(t)$ calculated by neglecting the second term in the above equation. For phase labeling in motion/displacement imaging, m(r) is preferably substantially equal to the magnetization $M_0$ to improve signal-to-noise ratio ("SNR") in phase-label measurements (and to avoid signal contributions from unlabeled magnetization components), and the small-tip-angle approximation is generally not sufficient. $M_{xy}$ and $B_1$ can be obtained from a series expansion, wherein a zeroth order term of $B_1$ is obtained from the small tip angle approximation, and higher order terms are obtained from lower order terms as follows:

$$\int_0^T B_{1,n}(t) e^{ir\cdot k(t)} dt =$$

$$-\frac{\gamma}{M_0} \sum_{j+l+m=n-1} \int_0^T d\tau B_{1,j}(\tau) e^{ir\cdot k(\tau)} \int_0^\tau \langle M_{xy,l}(r, s) \cdot iB_{1,m}(s) \rangle ds,$$

$$M_{xy,n}(r, t) = i\gamma M_0 \int_0^t B_{1,n}(\tau) e^{ir\cdot k(\tau)} d\tau +$$

$$i\gamma^2 \sum_{j+l+m=n-1} \int_0^t d\tau B_{1,j}(\tau) e^{ir\cdot k(\tau)} \int_0^\tau \langle M_{xy,l}(r, s) \cdot iB_{1,m}(s) \rangle ds,$$

wherein j, l m, and n are nonnegative integers, and n is the order of the term obtained, i.e., $B_{1,n}$ and $M_{xy,n}$ are nth order contributions to $B_1$ and $M_{xy}$, respectively. For a specified function $m(r)e^{if(r)}$, the series expansion can be calculated numerically until $M_{xy,n}(r,t)/M_0 \ll 1$, and the RF-gradient pulse combination is sufficiently approximated to produce a selected transverse magnetization $M_{xy}(r,T) = m(r)e^{if(r)}$.

Although phase labeling is described herein generally with respect to phase labeling with a single function f(r), multiple phase labels can be used to obtain a transverse magnetization $M_{xy}(r, T) = m_1(r)e^{if_1(r)} + m_2(r)e^{if_2(r)} + m_3(r)e^{if_3(r)} + \ldots + m_N(r)e^{if_N(r)}$ that is phase-labeled with respective functions $f_1(r)$, $f_2(r)$, $f_3(r)$, ..., $f_N(r)$.

The longitudinal magnetization $M_z$ can be phase-labeled in several ways. For example, a transverse magnetization $M^{xy}(r) = m(r)e^{if(r)}$ can be produced with an RF-gradient pulse combination as described above, and a second RF pulse such as a 90 degree pulse or other RF pulse applied along the y-axis. In this example, a 90 degree pulse is used and, for improved SNR, m(r) is configured to be substantially equal to the magnetization $M_0$ and the resulting longitudinal magnetization is $M_z = [m(r)e^{if(r)} + m(r)e^{-if(r)}]/2$.

Figure 3A:
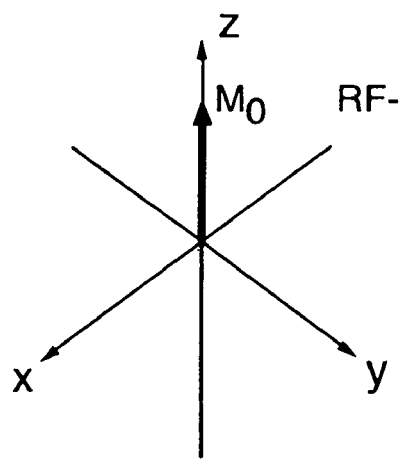
FIGS. 3A-3C illustrate phase labeling of a longitudinal and transverse magnetization based on a function f(r).
Figure 3B:
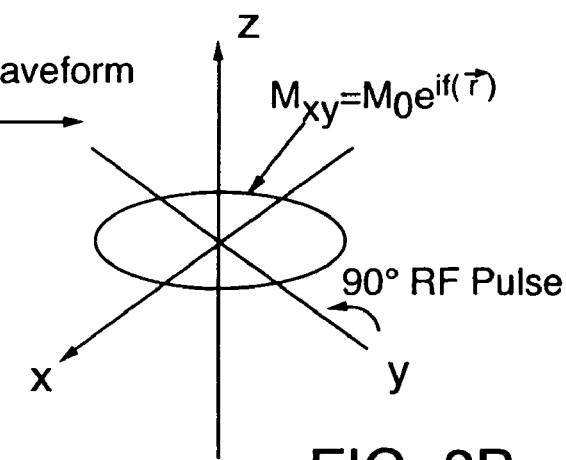
Figure 3C:
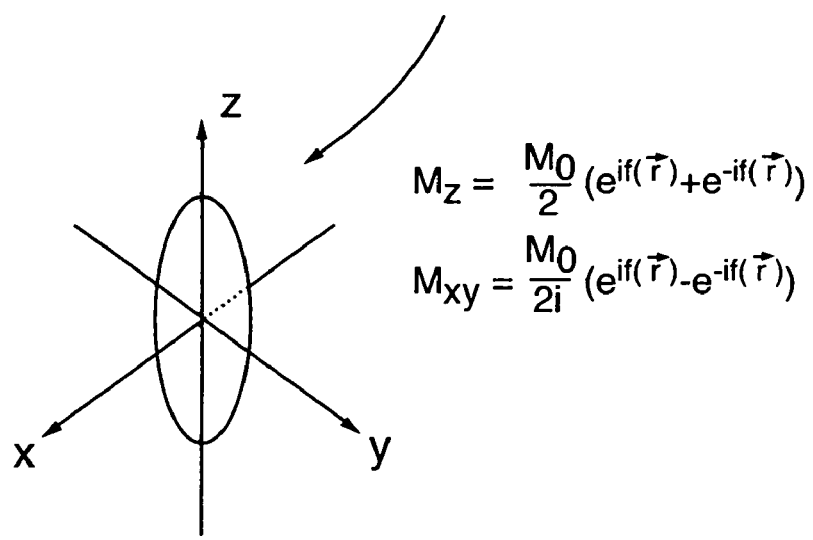

FIGS. 3A-3C illustrate phase labeling of longitudinal and transverse magnetizations with a specified function f(r). The initial magnetization is the axial magnetization $M_0$ as shown in FIG. 3A. An RF-gradient pulse combination is applied to rotate the magnetization $M_0$ into the transverse plane and produce a transverse magnetization $M_{xy} = M_0 e^{if(r)}$ as shown in FIG. 3B, leaving only a small (or no) z-component. A 90° RF pulse is applied along the y-axis, and an x-component of the magnetization is rotated into the yz-plane. The resulting longitudinal and transverse magnetizations, illustrated in FIG. 3C, are:

$$m_z = [e^{if(r)} + e^{-if(r)}] M_0 / 2, \text{ and}$$

$$M_{xy} = [e^{if(r)} - e^{-if(r)}] M_0 / (2i), \text{ respectively,}$$

and are both phase-labeled based on the function f(r).

Another method of producing phase-labeled terms $m(r)e^{if(r)}$ or $m(r)e^{-if(r)}$ in the longitudinal magnetization $M_z$ is to apply an RF-gradient pulse combination based on Pauly et al.'s small-tip-angle approximation.

Generally the RF-gradient pulse combinations produce phase modulations of the form $m(r)e^{if(r)}$ and $m(r)e^{-if(r)}$ on both the transverse and longitudinal magnetizations. As shown in FIG. 4A, an RF-gradient pulse combination is applied to rotate the magnetization $M_0$ into the xy-plane and produce a transverse magnetization $M_{xy} = M_0 e^{if(r)}$ and no axial magnetization. As shown in FIG. 4B, a 90° RF pulse is applied about an axis AX at an angle φ from the x-axis. A component of $M_{xy}$ perpendicular to the axis AX is rotated into a vertical plane at an angle φ relative to the x-axis and a component of $M_{xy}$ parallel to the axis AX remains in the xy-plane along the axis AX. The longitudinal and transverse magnetizations, illustrated in FIG. 4C, are $M_z = M_0 \{e^{i[f(r)-\Phi]} - e^{-i[f(r)-\Phi]}\}/(2i)$, and $M_{xy} = M_0 \{e^{i[f(r)-\Phi]} + e^{-i[f(r)-\Phi]}\}e^{i\Phi}/2$. The presence of the phase angle φ in the terms $e^{i[f(r)-\Phi]}$ and $e^{-i[f(r)-\Phi]}$ provides a method for separating these terms, i.e., by subtracting MRI signals that are acquired with $\Phi = \Phi_1$ and $\Phi = \Phi_2$.

Examples of Phase Labeling

In a first example, the selected function of displacement is equal to a Cartesian component of voxel displacement. For example, if the x-component is selected, the phase difference is proportional to $f(r(t_2)) - f(r(t_1)) = k(x(t_2) - x(t_1))$, wherein k is a nonzero constant. The corresponding phase label is the function $e^{ikx}$ and a transverse magnetization modulated with this phase label is produced by applying a 90° RF pulse (either slice-selective or volumetric) along the x-axis, followed by a gradient pulse along the x-axis and having an area corresponding to k. The resulting transverse magnetization is $M_{xy} = M_0 e^{ikx}$. Another 90° RF pulse is applied along the axis AX at an angle φ from the x-axis so that both $M_z$ and $M_{xy}$ include phase-labeled terms:

$$M_z = M_0 [e^{i(kx-\Phi)} - e^{-i(kx-\Phi)}]/(2i), \text{ and}$$

$$M_{xy} = M_0 [e^{i(kx-\Phi)} + e^{-i(kx-\Phi)}]/2.$$

Such phase labeling is readily configurable to phase modulate corresponding to a projection of the displacement vector along an arbitrary direction.

The function f(r) can also be specified in cylindrical, spherical, or other coordinates. As a second example, voxels can be phase labeled based on a radial displacement r in cylindrical coordinates with a function f(r)=kr, wherein k is a constant. The series expansion described above can be used to determine an appropriate RF-gradient pulse combination to produce $M_{xy}=m(r)e^{ikr}$. The resulting transverse magnetization $M_{xy}$ can be configured so that m(r)=0 for r=0 so that the Fourier transform of $M_{xy}$ is well defined and the series expansion for the RF-gradient pulse combination converges. As with the function kx in Cartesian coordinates, a 90° RF pulse is applied about an axis AX at an angle $\phi$ from the x axis after producing the transverse magnetization $M_{xy}=m(r)e^{ikr}$ so that both $M_z$ and $M_{xy}$ are phase-labeled:

$$M_z = M_0[e^{i(kr-\phi)} - e^{-i(kr-\phi)}]/(2i), \text{ and}$$

$$M_{xy} = M_0[e^{i(kr-\phi)} + e^{-i(kr-\phi)}]/2.$$

Such phase-labeling is especially useful for mapping changes in the diameter or size of an object relative to a central axis, such as measuring a radial contraction or dilation of a left ventricle of a heart.

The function f(r) can also be selected to be a function of the θ-coordinate (azimuthal angle) in a cylindrical coordinate system to label angular displacements, i.e., $\theta(t_2)-\theta(t_1)$. In a third example, a representative phase labeling function is f(r)=nθ, wherein n is a nonzero integer. Phase-labeling is performed as above except the RF-gradient pulse combination is determined using the function $m(r)e^{in\theta}$. This function is useful for mapping rotations, about a central axis. For example, such a function can be used in MRI of a cross-section of a left ventricle of the heart to produce images based on rotations of the left ventricle and angular changes in segments of the left ventricle.

Mapping the Time-Evolution of a Phase Label

The evolution of voxel phase after an initial phase labeling at time $t_1$ can be determined by detecting voxel phase at a subsequent time $t_2$. If the phase label is applied to the transverse magnetization as $M_{xy}=m(r)e^{if(r)}$, and the time period between $t_1$ and $t_2$ is short enough so that the transverse magnetization $M_{xy}$ does not entirely decay due to spin relaxation processes such as $T_2^*$ relaxation, then at time $t_2$ an image based on the transverse magnetization $M_{xy}$ can be directly acquired with standard gradient-recalled-echo (GRE) or spin-echo readout (SPE) methods, or variants such as spoiled gradient-recalled echo, fast-spin-echo, echo-planar, echo-train, k-space spiral scan, true free imaging in steady precession (FISP), and others. The spatial distribution of the phase of the transverse magnetization $M_{xy}$ corresponds to the phase label.

Figure 5:
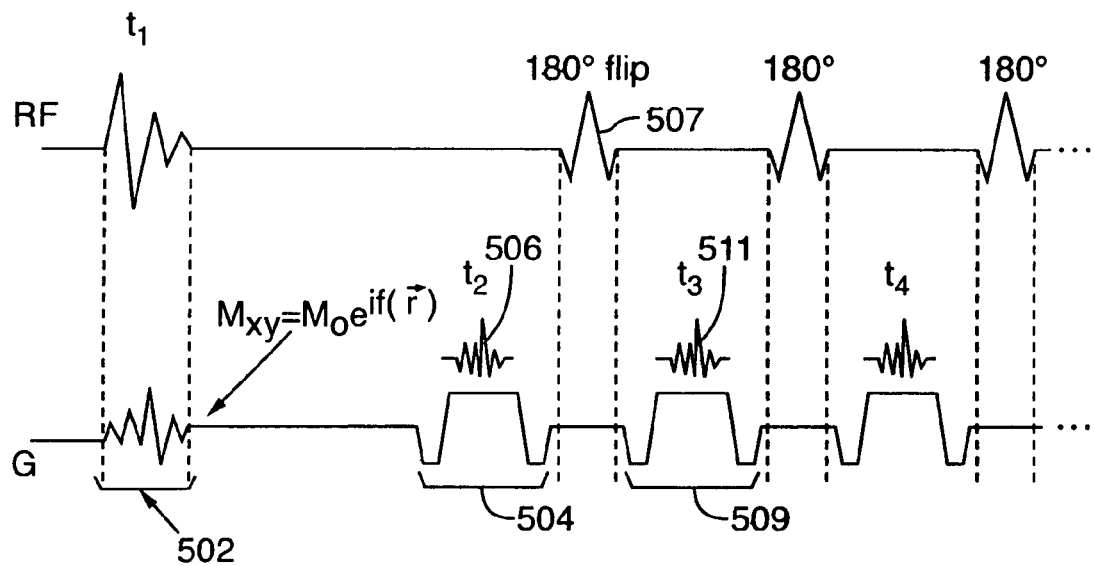
FIG. 5 illustrates RF and gradient (G) pulses applied in a fast spin-echo readout of a phase labeled transverse magnetization.

FIG. 5 illustrates acquisition of image data based on a phase-labeled transverse magnetization $M_{xy}$ using a fast spin-echo readout in which the transverse magnetization $M_{xy}$ is acquired at a series of times $t_n$. At a time $t_1$, an RF-gradient pulse combination 502 produces a transverse magnetization $M_{xy}=M_0 e^{if(r)}$ that is sampled at time $t_2$ by applying a fully balanced readout gradient pulse 504 to produce a first echo 506. The balanced readout gradient pulse 504 is compensated to produce no net phase shift. A 180° RF pulse 507 is then applied, followed by balanced readout gradient pulse 509, producing a second echo 511. The 180 degree RF pulse and the balanced readout gradient pulse are repeated, producing additional echoes.

Various exemplary acquisition methods are described herein that are suitable for measuring phase labeled transverse or longitudinal magnetizations (or both) that contain phase labels such as $e^{-if(r)}$ and $e^{if(r)}$. A phase-labeled longitudinal magnetization $M_z=[m(r)e^{i[f(r)-\phi]}-m(r)e^{-i[f(r)-\phi]}]/(2i)$ at time $t_1$ can be detected by applying an RF-gradient pulse combination at a time $t_2$ to produce a spatial phase distribution $A(r)=a(r)e^{-if(r)}$, wherein a(r) is a real function of position r. The spatial phase distribution A(r) provided by the RF-gradient pulse combination is selected to correspond to the phase-label applied at time $t_1$. Such RF-gradient pulse combinations can be selected using the series expansion described above. The resulting transverse magnetization is:

$$M_{xy}(r)=a(r)\{m(r)e^{i[f(r(t1))-f(r(t2))-\phi]}-m(r)e^{-i[f(r(t1))+f(r(t2))-\phi]}\}/(2i).$$

For some phase-labeling functions f(r), the two terms in the above equation have little overlap in Fourier transform space ("k-space"), and data corresponding to the first term can be isolated by acquiring $M_{xy}(r)$ over a k-space region encompassing primarily the first term. The acquisition can be of any of the standard gradient-recalled echo or spin-echo schemes, or variants thereof. The phase of the first term in $M_{xy}$ includes f(r')−f(r). The RF-gradient pulse combination that produces A(r) is referred to as a "decoding pulse."

Figure 6:
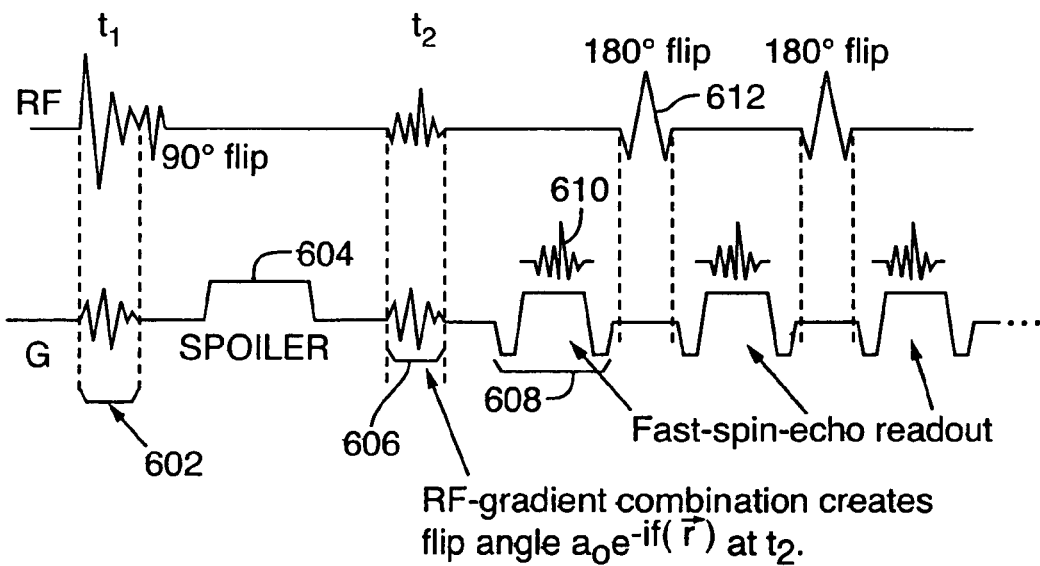
FIG. 6 illustrates RF and gradient (G) pulses applied in a fast spin-echo readout of a phase labeled longitudinal magnetization.

FIG. 6 illustrates data acquisition using a decoding pulse and a fast spin-echo readout. At time $t_1$, an RF-gradient pulse combination 602 produces a phase-labeled transverse magnetization $M_z=[e^{if(r)}-e^{if(r)}-e^{-if(r)}]M_0/(2i)$. A spoiler gradient pulse 604 is applied to dephase the coherent transverse magnetization. At time $t_2$, an RF-gradient decoding pulse 606 produces a tip angle of the spatial distribution $a_0 e^{if(r)}$. The resulting transverse magnetization is:

$$M_{xy}(r)=a_0 M_0 \{e^{i[f(r(t1))-f(r(t2))]}-e^{-i[f(r(t1))+f(r(t2))]}\}/(2i).$$

This magnetization is then sampled with a fully balanced readout gradient pulse 608 to produce an echo 610. A 180° RF pulse 612 is applied, changing the sign of the phase factors in the transverse magnetization so that $M_{xy}(r)$ is:

$$M_{xy}(r)=a_0 M_0 \{e^{-i[f(r(t1))-f(r(t2))]}-e^{i[f(r(t1))+f(r(t2))]}\}/(2i)$$

and the balanced readout gradient pulse/180° RF pulse sequence is repeated. If the two terms in $M_{xy}$ have little k-space overlap, only the area of k-space encompassing the first term is sampled. To compensate for sign changes of the phase factors produced by 180° RF pulses, a complex conjugate of data from every other readout period is obtained and assigned to an opposite location in k-space.

As shown in FIG. 6, between times $t_1$ and $t_2$, the spoiler pulse 604 is applied to destroy the coherence in $M_{xy}$ left by the RF-gradient pulse combinations at time $t_1$. Alternatively, if the time period between $t_1$ and $t_2$ is sufficiently long so that the coherence in $M_{xy}$ decays to negligible levels, then such a spoiler gradient pulse is unnecessary.

Figure 7:
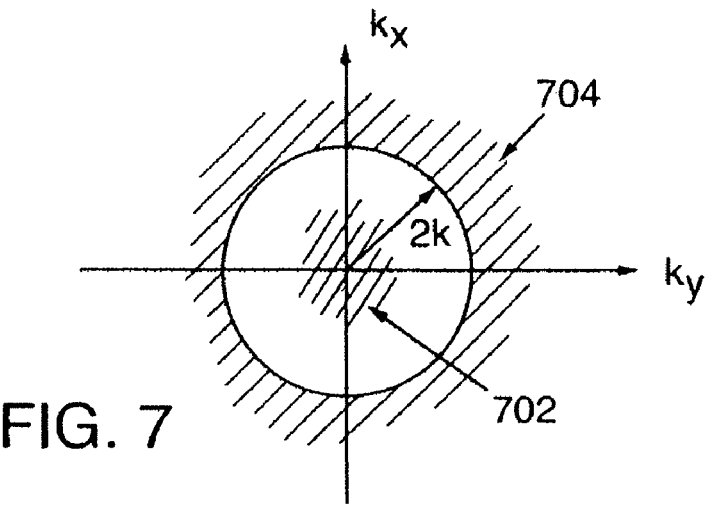
FIG. 7 is an illustration of k-space regions corresponding to phase factors of a transverse magnetization.

This acquisition method can be further illustrated with the example of the phase-labeling function f(r)=kr, in cylindrical coordinates. After the decoding RF-gradient pulse combination that produces A(r) is applied, the terms in $M_{xy}$ have phase factors $e^{i[k(r(t1)-r(t2))-\phi]}$ and $e^{i[k(r(t1)+r(t2))-\phi]}$. If the specimen does not experience large or abrupt deformations or displacements, changes, but a continuous or gradual deformation, the second term oscillates radially at a high spatial frequency of approximately 2 k, while the first term has a nearly zero frequency oscillation. Referring to FIG. 7, the Fourier transform of the first term is concentrated at k=0 in a region 702, while the Fourier transform of the second term is at a distance greater than or equal to 2 k from the origin in a region 704. If k is sufficiently large, these two regions have little or no overlap in k-space. In MRI, sampling $M_{xy}(r)$ with a series of readout gradients is equivalent to sampling the Fourier transform of $M_{xy}(r)$ in k-space. Therefore, $M_{xy}(r)$ can be sampled in k-space near the origin (k=0) to include contributions from the term having phase factor $e^{i[k(r(t1)-r(t2))-\Phi]}$. After an inverse Fourier transform, the corresponding image includes contributions based on $k(r(t_2)-r(t_1))$.

Generally, by using an RF-gradient pulse combination A(r) to tip the magnetization $M_z$ onto the xy plane and selecting a phase of A(r) to have a sign opposite that of one of the phase-labeled terms in $M_z$, the phase of a magnetization tipped onto the transverse plane contains $f(r(t_2))-f(r(t_1))$. By acquiring data corresponding to this term, images based on $f(r(t_2))-f(r(t_1))$ can be produced.

Figure 8:
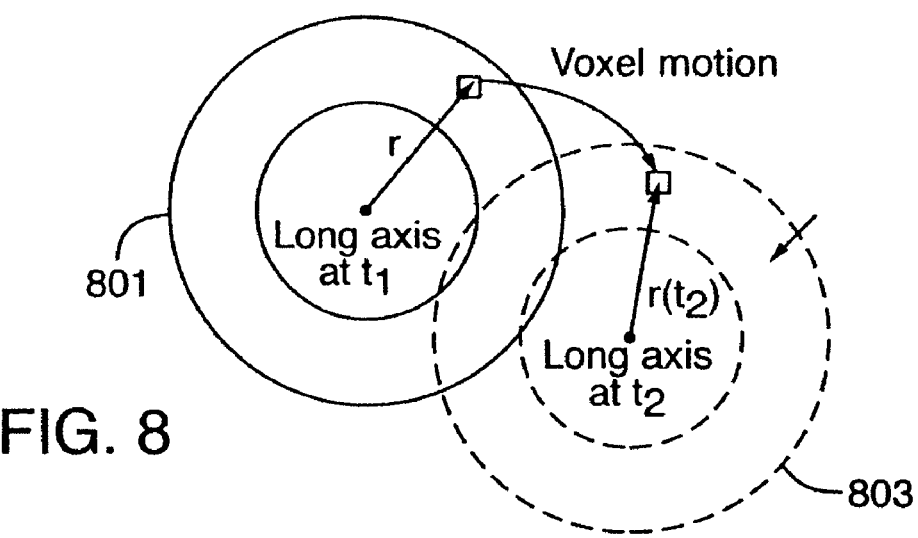
FIG. 8 illustrates voxel motion with respect to a nonstationary coordinate system.

In the above example, $k(r(t_2)-r(t_1))$ is proportional to the radial distance change between the voxel and the central axis. In certain applications, such as mapping the radial contraction and dilation of the left ventricle relative to a long axis of the left ventricle, the position of the long axis generally changes with time as is illustrated in FIG. 8. In this case, a prior MRI scan can be used to locate ventricle positions 801, 803 at times $t_1$ and $t_2$, respectively. Then, the RF-gradient pulse combination that applies the selected phase label can be calculated with respect to the axis position at the initial time $t_1$, while the decoding RF-gradient pulse combination can be calculated with respect to the axis position at the time of decoding. Then, $r(t_1)$ and $r(t_2)$ are radial distances to the long axis of the left ventricle at times $t_1$ and $t_2$ points from the same voxel of the myocardium, and $k(r(t_2)-r(t_1))$ represents radial dilation/contraction regardless of the translational movement of the heart.

Data can also be acquired based on a phase-labeled longitudinal magnetization, such as $M_z=\{m(r)e^{i[f(r)-\Phi]}-m(r)e^{-i[f(r)-\Phi]}\}/(2i)$. Between times $t_1$ and $t_2$, a series of spoiler gradient pulses (or a single spoiler pulse) is applied to reduce or eliminate coherence in the transverse magnetization left by the encoding RF gradient pulse combination at $t_1$. Alternatively, if the time period between $t_1$ and $t_2$ is sufficiently long so that the coherence in $M_{xy}$ decays to negligible levels, then the spoiler gradient pulses are not needed. At time $t_2$, a standard MRI sequence (e.g., GRE or SPE) is used to acquire an image based on the transverse magnetization of $M_{xy}$. Then another phase labeling is performed with a different phase constant $\phi'$ by changing the direction of the RF pulses and another image based on the transverse magnetization $M_{xy}$ is acquired the same way. Denoting the original voxel position as $r(t_1)=r'$, then $$M_{xy,1}(r(=\{m(r')e^{i[f(r')-\Phi]}-m(r')e^{-i[f(r')-\Phi]}\}/(2i) \text{ and}$$

$$M_{xy,2}(r)=\{m(r')e^{i[f(r')-\Phi']}-m(r')e^{-i[f(r')-\Phi']}\}/(2i).$$

Based on these equations, $m(r')e^{if(r')}e^{if(r')}$ can be determined as $$m(r')e^{if(r')}=[M_{xy,2}(r)e^{i\Phi}-M_{xy}(r)e^{i\Phi'}]/\sin(\phi-\phi'),$$

and therefore the phase-label function f(r) can be obtained as the phase of $m(R')e^{if(r')}$ and the function of displacement f(r')-f(r) can also be obtained. This method is particularly suited to phase labels such as $e^{in\theta}$ for which modulations corresponding to the phase labels $e^{-if(r)}$ and $e^{if(r)}$ are not well separated in k-space.

Phase-labeled Longitudinal Magnetization Acquisition Method

The longitudinal magnetization can be phase labeled to be $M_z=\{m(r)e^{i[f(r)-\Phi]}-m(r)e^{-i[f(r)-\Phi]}\}/(2i)$ at time $t_1$. Between times $t_1$ and $t_2$, a series of spoiler gradient pulses can be applied to destroy the coherence in $M_{xy}$ left by the encoding pulses at $t_1$. Alternatively, if the time period between $t_1$ and $t_2$ is sufficiently long so that the coherence in $M_{xy}$ decays to negligible levels, then the spoiler gradient pulses are not needed. If the two terms in $M_z$ have little overlap in k-space, as for example in $f(r)=k_x x+k_y y$ where $k_x$ and $k_y$ are large, then at time $t_2$, a standard GRE or SPE method or their variants can be used to acquire a region in k-space that encompasses both terms. The two terms are then reconstructed from their respective regions in k-space. The phase factor $e^{if(r')}$ can then be obtained from either one of two terms, or from the phase difference between the two terms. Once f(r') is known, the desired function of displacement f(r')-f(r) is obtained. The two phase-labeled terms $m(r)e^{if(r)}$ and $m(r)e^{-if(r)}$ are conventionally called a stimulated echo (STE) and a stimulated anti-echo (STAE).

If the two terms in $M_z$ are sufficiently separated in k-space, a gradient-recalled echo method or a modified spin-echo readout method, or their variants, can also be used to collect only the region in k-space that corresponds to one of the two terms. The phase of this single term then contains f(r'), and the desired function f(r')-f(r') can be obtained.

Example Mapping of Phase Label Time Evolution

Phase labels can be mapped as a function of time to track motion tracking over a period of time. At each time point after the initial phase labeling, a fraction of the longitudinal magnetization is tipped onto the transverse plane, and the resulting transverse magnetization is detected with any of the methods described herein. After data acquisition, the remaining transverse magnetization can be destroyed with gradient spoiler pulses, and this procedure repeated again. The process can be repeated until the phase-labeled longitudinal magnetization is expended. To ensure that only a fraction of the phase-labeled $M_z$ is used each time, the tip angle of the decoding RF-gradient pulses preferably small compared to 90°, e.g., 30°.

For such motion tracking, the phase labeling is performed with a 90° RF pulse, a gradient pulse along the x direction, and a second 90° pulse. This creates the longitudinal magnetization $M_z=(e^{ikx}-e^{-ikx})M_0/(2i)$. A spoiler gradient pulse is then applied to destroy the coherent transverse magnetization. At time $t_2$, a small flip angle $\alpha$ pulse tips a portion of the longitudinal magnetization into the transverse plane, where it is sampled repeatedly with a fast spin-echo readout scheme. The readout gradient waveforms of the fast spin-echo scheme are fully balanced to avoid any phase addition to the phase-label function. Then a spoiler gradient can be applied to crush any residual transverse magnetization, before this process is repeated again for the next time point. This process is repeated for a series of time points, until the phase-labeled terms in the longitudinal magnetization are exhausted.

Example Mapping of Displacement with Phase Labeling

A specific example of phase labeling is described with reference to cardiac functional imaging based on displacement encoding with stimulated echoes ("DENSE"). A phase labeling function f(r) is selected that is a dot product of r and a vector k such that the phase-labeling function is $f(r)=k_x x+k_y y+k_z z$, wherein $k_x$, $k_y$, and $k_z$ are constants. Phase-labeled terms corresponding to $m(r)e^{if(r)}$ and $m(r)e^{if(r)}$ are referred to as a stimulated echo ("STE") and a stimulated anti-echo ("STAE"). A stimulated echo is generally compensated for phase shifts caused by magnetic field inhomogeneity, chemical shifts, and off-resonance effects and is nearly equivalent to a spin-echo except for the signal loss due to $T_1$ during a mixing time ("TM"). In order to acquire an STE, two gradient field pulses of equal gradient moment and of the same polarity are used during the echo time ("TE"). In contract, a stimulated anti-echo (STAE) can be produced with gradient pulses of opposite polarities. An STAE resembles a gradient-recalled echo instead of a spin-echo and carries phase accumulated due to magnetic field inhomogeneities, chemical shifts, and off-resonance effects.

Figure 9:
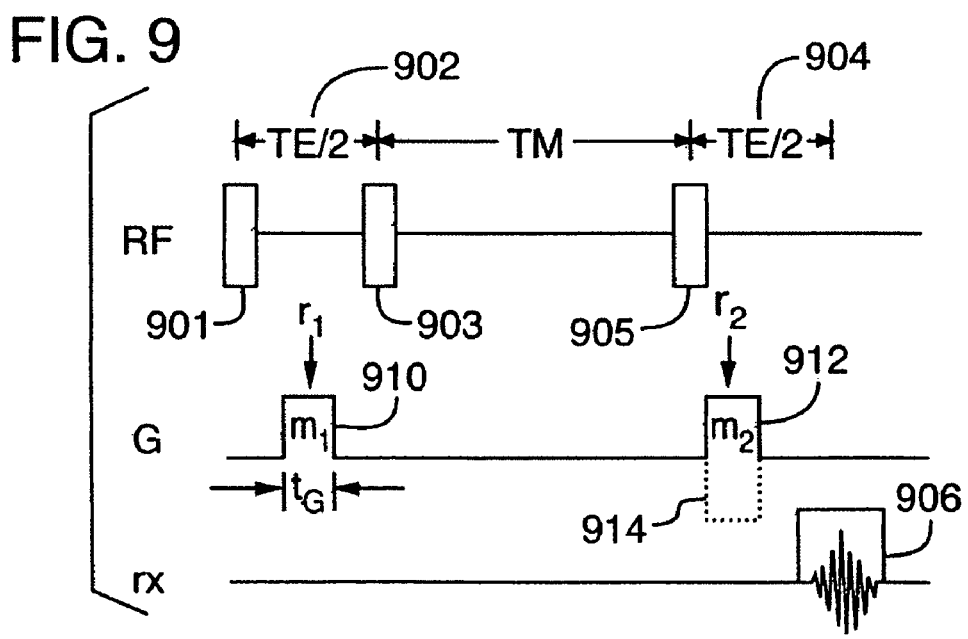
FIG. 9 illustrated RF and gradient pulses applied to produce a signal (rx) from a phase labeled specimen, wherein the signal corresponds to a stimulated echo or stimulated anti-echo.

Referring to FIG. 9, a magnetization vector M is first tipped onto the transverse plane with a first 90° pulse 901. The magnetization M is described in a complex representation:

$$M[\cos(\Phi)+i\sin(\Phi)]=Me^{i\Phi} \quad [1]$$

wherein M is an amplitude and $\phi$ a phase of the magnetization M as it precesses onto the xy-plane. In the laboratory frame of reference, the phase $\phi$ in is given by:

$$\Phi=\gamma B_0 t+\omega_{OFF} t+\gamma \Delta B_0 t+\gamma m r \quad [2]$$

wherein $\omega_{OFF}$ is the off-resonance offset, $\Delta B_o$ is an inhomogeneity in $B_0$, and m is a gradient field moment or area. In this example, the gradient field moment is defined as $m=Gt_G$ wherein G is the amplitude of an equivalent rectangular gradient pulse and $t_G$ is a pulse duration of the equivalent pulse. In the rotating frame of reference, $\gamma B_o t$ is zero. Off-resonance, main field inhomogeneity and chemical shift phase accumulations have similar time dependence and a total S of these phase shifts is:

$$S=\omega_{OFF} t+\gamma \Delta B_0 t. \quad [3]$$

Therefore, in the rotating frame of reference, the total phase is:

$$\phi=S+\gamma mr. \quad [4]$$

During STEAM imaging, all 90° pulses are applied along the same axis (for example along +y), during the first half 902 of an echo time (TE/2) and a phase $$\Phi_1=S_1+\gamma m_1 r_1 \quad [5]$$

accumulates. A second 90° pulse 903 rotates a component of magnetization perpendicular to $B_1$, (the x-component) back to the z-axis. Gradient spoiler pulses (not shown in FIG. 9) applied during the mixing time TM scramble components of magnetization remaining in the transverse plane. Because the gradient pulse 910 during the first half of the echo time TE distributes the magnetization components evenly between the real (x) and the imaginary (y) axes, one half of the magnetization is lost. The magnetization relaxes with time constant $T_1$. In addition, the phase of the scrambled portion is lost, and a direction of precession of the magnetization can no longer be uniquely determined. If an imaginary part of the magnetization is scrambled and lost (i.e., a y-component), only $M\cos(\Phi_1)=M\cos(S_1+\gamma m_1 r)$ is restored onto the transverse plane following a third 90° RF pulse 905. This magnetization can be written as $$M\cos(\varphi_1) = \frac{M}{2}e_1^{i\varphi} + \frac{M}{2}e_1^{-i\varphi} = \quad [6]$$

-continued $$\frac{M}{2}[\cos(\varphi_1)+i\sin(\varphi_1)] + \frac{M}{2}[\cos(-\varphi_1)+i\sin(-\varphi_1)]$$

The nonscrambled real portion of the signal along the x-axis can be considered as the sum of two vectors precessing at the same rate, but in opposite directions. Each of them has half the amplitude of the original magnetization vector.

The magnetization described by Equation 6 is missing phase imparted to the spins by the 90° pulses. For this description of STEAM, the second and third 90° pulses in the RF pulsing scheme (90°$_y$–90°$_y$–90°$_y$) behave as a 180° pulse because the magnetization rotates 180° as a result of their application. A 180° pulse changes the sign of the phase since the signal is multiplied by $e^{-i}$. After the application of a 180° pulse, the resulting magnetization is the complex conjugate of the original magnetization, i.e., its phase changes sign. For an RF pulse scheme 90°$_y$–90°$_y$–90°$_y$, there is no sign change. After the 90° pulse 905, the phase of the magnetization is:

$$\Phi_1=-S_1-\gamma m_1 r_1 \quad [6a]$$

During the second half 904 of the echo time TE an additional phase $\phi_2$ accumulates, wherein $$\Phi_2=+S_2+\gamma m_2 r_2. \quad [7]$$

At a center of an acquisition window 906, the transverse magnetization is:

$$M\cos(\varphi_1)e^{i\varphi_2} = \left\{\frac{M}{2}e^{i\varphi_1} + \frac{M}{2}e^{-i\varphi_2}\right\}e^{i\varphi_2} = \quad [8]$$

$$\frac{M}{2}e^{i(\varphi_1+\varphi_2)} + \frac{M}{2}e^{i(-\varphi_1+\varphi_2)} = \frac{M}{2}[\cos(\varphi_1+\varphi_2)+i\sin(\varphi_1+\varphi_2)] +$$

$$\frac{M}{2}[\cos(-\varphi_1+\varphi_2)+i\sin(-\varphi_1+\varphi_2)]$$

Gradient pulses 910, 912 are characterized by respective amplitudes $m_1$, $m_2$ and a duration $t_G$. Typically, $m_1=m_2$ and $S_1=S_2$ since the echo interval TE is divided into two equal parts. Therefore, for stationary spins, $\phi_1+\phi_2=0$ and $(-\phi_1+\phi_2)=2S_1+2\gamma m_1 r_1$. The detected signal is obtained from the magnetization $$\frac{M}{2} + \frac{M}{2}[\cos(2S_1+2\gamma m_1 r_1)+i\sin(sS_1+2\gamma m_1 r_1)] \quad [9]$$

The signal consists of two parts. The first part corresponds to an STE since no residual phase exists as a result of the time-dependent terms described by S and resembles a spin-echo. The second part is modulated by twice the phase imparted by the gradient moment $m_1$. In imaging experiments, $m_1$ is typically large enough to shift this component outside the region of k-space sampled to create an image. Otherwise, banding artifacts can appear. For non-stationary spins $(r_2=r_1+\delta)$, then $\phi_1+\phi_2=\gamma m_1\gamma$ and $(-\phi_1+\phi_2)=2S_1+2\gamma m_1 r_1+\gamma m_1 \delta$. Therefore, the detected signal consists of a DENSE signal and an $m_1$ modulated component that is filtered out. The DENSE signal is:

$$\frac{M}{2}[\cos(\gamma m_1 \delta) + i\sin(\gamma m_1 \delta)] = \frac{M}{2}e^{i\gamma m_1 \delta}. \quad [10]$$

On the other hand, if two gradient pulses 910, 914 of opposite signs are applied, the signals changes. With stationary spins $m_1 = -m_2$, and $S_1 = S_2$, then $\phi_1 + \phi_2 = 2\gamma m_1 r_1$ and $(-\phi_1 + \phi_2) = 2S_1$. Therefore, the signal detected is an STAE and corresponds to:

$$\frac{M}{2}[\cos(-2\gamma m_1 r_1) + i\sin(-2\gamma m_1 r_1)] + \frac{M}{2}[\cos(2S_1) + i\sin(2S_1)]. \quad [11]$$

A filter prior to a Fourier transform removes signal contributions modulated by $m_1$. The remaining signal portion is modulated by the time-varying terms (S) such as field inhomogeneity, etc., and is similar to a gradient-echo. If the spins are not stationary ($r_2 = r_1 + \delta$), then $\phi_1 + \phi_2 = -2\gamma m_1 r_1 - \gamma m_1 \delta$, and $(-\phi_1 + \phi_2) = 2S_1 - \gamma m_1 \delta$. Thus, the signal portion that is passed by the Fourier transform filter is an STAE and corresponds to:

$$\frac{M}{2}[\cos(2S_1 - \gamma m_1 \delta) + i\sin(2S_1 - \gamma m_1 \delta)] = \frac{M}{2}e^{i(2S_1 - \gamma m_1 \delta)}. \quad [12]$$

The STAE in a DENSE experiment reflects displacement $\delta$ that occurs between the two gradient pulses in the TE period but it is contaminated by the time varying terms (S). This is the reason for selecting the STE not the STAE as the STEAM signal when performing such measurements. The STE is not totally free of influence by the time-varying terms. Because the spins move, the contributions of these terms during the first half 902 of TE are not equal to those during the second half 904 of TE. In a more accurate description, $S_1 \neq S_2$.

To describe phase label measurements, phases of two components of the signal magnetization can be written as ordered pairs. For example, the signal stored along the longitudinal axis after the second 90° pules, as described by Equations 5 and 6, can be expressed as $$\{\Phi_1, -\Phi_1\} = \{S_1 + \gamma m_1 r_1, -S_1 - \gamma m_1 r_1\} \quad [12a]$$

Referring to FIG. 9, the signal magnetization after the gradient pulse 912 is described by Equation 9 and can be written as $\{0, 2S_1 + 2\gamma m_1 r_1\}$. In the case of moving spins, where $S_1 \neq S_2$ and $r_2 = r_1 + \delta$, the STE can be written as:

$$\{-S_1 + S_2 + \gamma m_1 \delta_1, S_1 + S_2 + \gamma m_1 \delta + 2\gamma m_1 r_1\} \quad [13]$$

As discussed previously, only the first term is detectable while the second is modulated by $2\gamma m_1 r_1$ and is filtered out before the Fourier transform. The detected portion corresponds to an STE. A more complete description of a STEAM signal in the presence of motion and gradient pulses of opposite polarity is:

$$\{-S_1 + S_2 - 2\gamma m_1 r_1 - \gamma m_1 \delta, S_1 + S_2 - \gamma m_1 \delta\} \quad [14]$$

The first term is undetectable since it is modulated by $\gamma m_1 r_1$, while the second term corresponds to an STAE.

The fast spin echo (FSE) measurement shown in FIG. 9 can cause severe image artifacts when used to rapidly sample a STEAM signal because the signal phase changes sign with every 180° pulse. These image artifacts can be avoided with a dual echo method.

Figure 10:
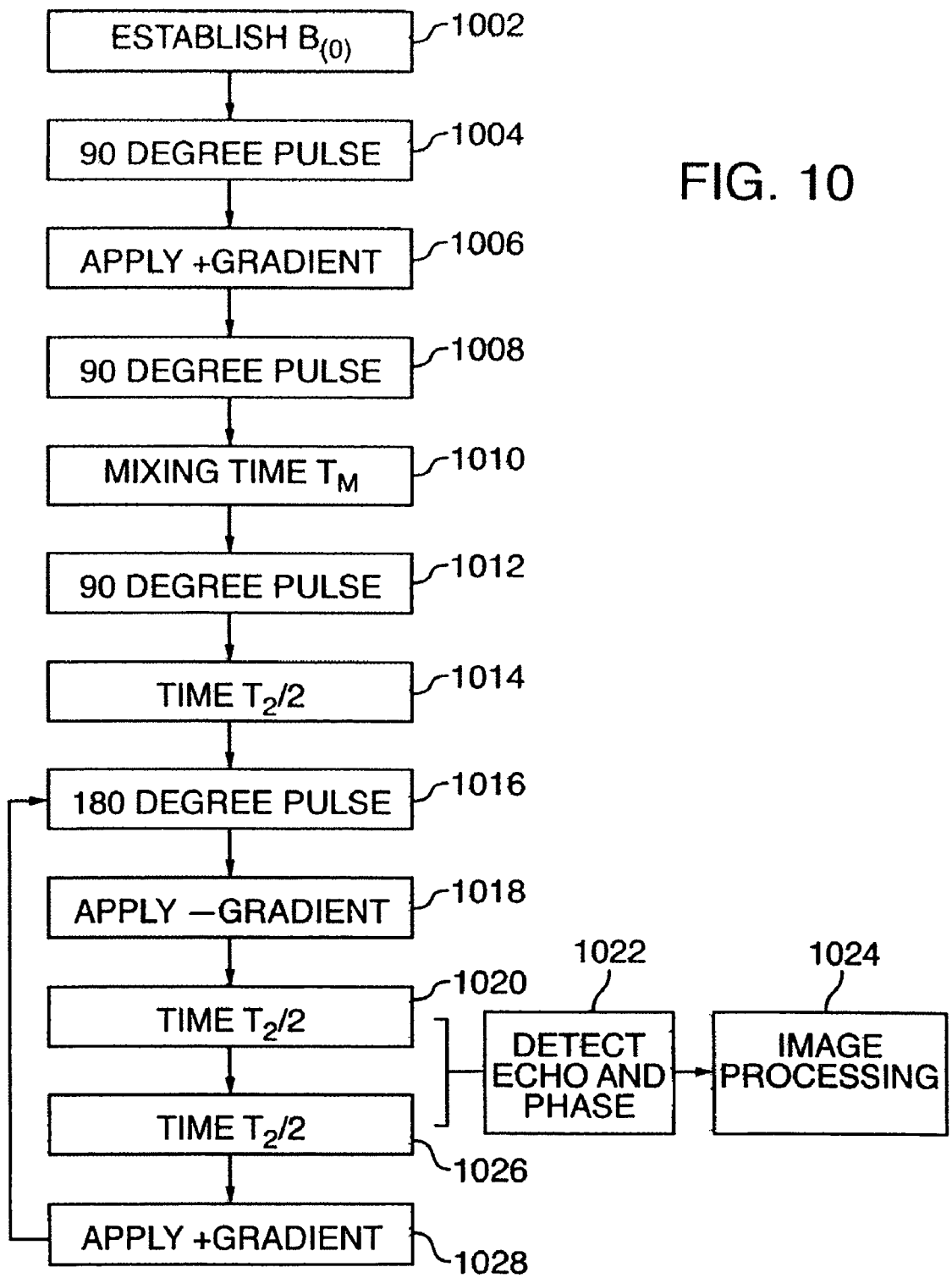
FIG. 10 is a block diagram of a dual echo imaging method.

FIG. 10 is a block diagram of a dual echo method of displacement imaging. An axial magnetic field $B_0$ is established in a step 1002 to produce a +z-directed magnetization $M_0$. In a step 1004, a 90 degree pulse is applied with the y-axis as the axis of rotation, rotating the magnetization $M_0$ to the x-axis. A magnetic field gradient $+G_x$ is applied in a step 1006 for a duration $t_G$, shifting the Larmor frequency by $\gamma G_x x_1$. This frequency shift produces a phase shift proportional to $\gamma G_x t_G x = \gamma m_1 x_1$ where $m_1 = G_x t_G$; and rotates the magnetization $M_0$ from the x-axis by an angle $\gamma m_1 x_1$. In addition, during $t_G$ an additional time-dependent phase shift $S_1$ is produced by an off-resonance frequency offset $\omega_{OFF}$, and the inhomogeneity $\Delta B_0$ in the axial field $B_0$ and the phase shift $S_1 = \omega_{OFF} t_G/2 + \gamma \Delta B_0 t_G/2$. Upon completion of the step 1006, the magnetization is in the transverse plane and is represented as $M_0 \exp[i(\gamma m_1 x_1 + S_1)]$. In a step 1008, a second 90 degree pulse is applied along the y-axis to rotate an x-component (i.e., the real part) of the magnetization $M_0 \exp[i(\gamma m_1 x_1 + S_1)]$ to the z-axis and a y-component of the magnetization is unchanged. Typically, the y-component decays rapidly with a time constant referred to as $T_2^*$. As a result of the second 90 degree pulse and the decay of the y-component of magnetization, the remaining magnetization is z-directed with a magnitude that is proportional to $M_0 \cos(\gamma m_1 x_1 + S_1)$. For convenience, $\cos(\Phi_1 + S_1)$ can be expressed as a sum of complex exponentials so that the magnetization is $M_0 [\exp i(\Phi_1 + S_1) + \exp{-i(\Phi_1 + S_1)}]/2$.

In a step 1010, a mixing time $T_M$ is provided in which no additional magnetic fields are applied. During the mixing time $T_M$, dipole moments associated with moving voxels of the sample experience displacements. After the mixing time $T_M$, a third 90 pulse is applied in a step 1012, rotating the magnetization vector back into the transverse plane. A first compensation interval of duration $t_2/2$ is provided in a step 1014. During the first compensation interval, no additional magnetic fields are applied but a phase shift $S_2$ is produced by the off-resonance frequency offset $\omega_{OFF}$ and the magnetic field inhomogeneity $\Delta B_0$. The phase shift $S_2 = \omega_{OFF} t_2/2 + \gamma \Delta B_0 t_2/2$.

A 180 degree pulse is applied in a step 1016, rotating the magnetization in the xy-plane such that the x-component experiences a 180° phase shift. A magnetic field gradient of magnitude $-G$ is then applied for a duration $t_G$ in a step 1018 and produces a phase shift proportional to $-Gt_G x = -\gamma m_2 x_2$. A second compensation interval $t_2/2$ is provided in a step 1020. An echo is detected in a step 1022 and data are processed in a step 1024.

In a step 1026, a compensation interval $t_2/2$ is provided and in a step 1028 a gradient $+G$ is applied for a duration $t_G$. Steps 1026, 1028, 1018, 1020 are repeated to provide additional echos in order to form an image. The number of echos is limited by $T_2$ relaxation.

Table 1 illustrates the phase shifts produced by the method of FIG. 10, wherein $\cos\Phi$ is represented as a sum of $\exp(-i\Phi)$ and $\exp(i\Phi)$.

TABLE 1

Phase shifts associated with the method of FIG. 10 for $m_1 = m_2$.

| Step No. | Phase Source | −phase term | +phase term |
|---|---|---|---|
| 1012 | 90 degree pulse | $-S_1 - \gamma m_1 x_1$ | $S_1 + \gamma m_1 x_1$ |
| 1014 | $t_2/2$ | $-S_1 + S_2 - \gamma m_1 x_1$ | $S_1 + S_2 + \gamma m x_1$ |
| 1016 | 180 degree pulse | $S_1 - S_2 + \gamma m_1 x_1$ | $-S_1 - S_2 - \gamma m_1 x_1$ |
| 1018 | −gradient | $S_1 - S_2 - \gamma m\delta$ | $-S_1 - S_2 - \gamma m\delta - 2\gamma mx$ |
| 1020 | $t_2/2$ | $S_1 - \gamma m\delta$ | $-S_1 + \gamma m\delta - 2\gamma mx_2$ |
| 1022 | | Echo | |
| 1026 | $t_2/2$ | $S_1 + S_2 - \gamma m\delta$ | $-S_1 + S_2 + \gamma m\delta - 2\gamma mx_2$ |
| 1028 | +gradient | $S_1 + S_2 + \gamma m x_1$ | $-S_1 + S_2 - \gamma m x_1$ |
| 1016 | 180 degree pulse | $-S_1 - S_2 - \gamma m x_1$ | $S_1 - S_2 + \gamma m x_1$ |
| 1018 | −gradient | $-S_1 - S_2 + \gamma m\delta - 2\gamma m_1 x_2$ | $S_1 - S_2 - \gamma m\delta$ |
| 1020 | $t_2/2$ | $-S_1 + \gamma m\delta - 2\gamma m_1 x_2$ | $S_1 - \gamma m\delta$ |
| 1022 | | | Echo |

While the echos are contaminated by $S_1$, the $S_2$ contributions are cancelled. The procedure of Table 1 and FIG. 10 continues until limited by a transverse relaxation time $T_2$ or other relaxation time. In the step 1022, the echo is associated with either the $+i\Phi$ or $-i\Phi$ phase terms and added to a corresponding image.

Simultaneous Dual-Echo Readout for STEAM

The readout scheme presented above has the advantage of utilizing the full extent of the available magnetization for collecting data by sampling either the STE or the STAE at any given acquisition window. In addition, it requires no special post-processing tools when compared to existing slower versions of DENSE. However, this scheme lacks the ability of simultaneously sampling both components (STE and STAE) of the signal. By eliminating the second gradient encoding pulse (see FIG. 11B), both components can be sampled within the same acquisition window. The two components are separated in k-space by a distance of $2\gamma m_1 r_1$. Therefore, the acquisition window is extended to accommodate both components. Its actual duration will depend on the desired imaging parameters (such as field of view ("FOV"), sampling speed, image resolution) and the encoding strength utilized. Since both components are rephased off-center within the acquisition period, a linear phase gradient will exist across the FOV of the image reconstructed from either component. In order to estimate this phase gradient and compensate for its effects via the image reconstruction algorithm, the gradient moment $m_1$ is preferably compared to the area of the readout gradient pulse contained between two successive sampled points. Since this area of $G_x/BW$ corresponds to a maximum of $2\pi$ phase evolution, the overall phase gradient across the FOV can be estimated and corrected for. However, in practice, hardware limitations can cause additional phase gradients across the FOV and therefore it is preferable to measure the phase gradient from an immobile structure within the image, such as a representation of the liver margin, and adjust the correction factor accordingly. Once the phase gradient has been corrected in both images acquired from the two signal components (STE and STAE), the displacement information can be combined to yield a single dataset that possesses a higher signal-to-noise ratio. The resulting dataset will be contaminated by the time varying phase terms, $S_1$, by twice as much when compared to the STE alone.

Decoupling Overlapping STE and STAE in the Acquisition Window

In both acquisition schemes described above, it is assumed that the two echoes (STE and STAE) are separated in k-space adequately by means of the encoding gradient moment, $m_1$, in order to avoid overlap of the two signal components. Such overlap can result in high-frequency content contamination during signal sampling and therefore diminished edge definition in the images. Unless such a penalty is acceptable, the two echoes are preferably separated by at least $\gamma N_x G_x/BW$, where $N_x$ is the number of points along the x-direction. This translates to utilizing encoding gradient strengths (measured in mm/π) of less than half the pixel size. This is true because the encoding gradient strength, Enc, is described by $$Enc = \frac{1}{m_1 \cdot 2 \cdot 4250 \cdot 10^{-7}}$$

while the pixel size, p, is $$p = \frac{1}{m_{READ} \cdot 4250 \cdot 10^{-7}}$$

and $$m_1 \geq m_{READ}$$

With some encoding schemes, it is not always possible to utilize encoding pulses that will lead to such clear separation between the two components of the signal. A mechanism for distinguishing the two components in such cases is described below. For this description, it is assumed that the free induction decay ("FID") has been suppressed.

For example, with the STEAM pulse sequence, the application of the gradient encoding pulse, with moment $m_1$, results in imparting phase to the spins according to their position in space. As such, the net $M_{XY}$ magnetization is scrambled across the xy-plane on both the x and y-axes. As a result, the second 90° RF pulse can only nutate back to the longitudinal axis half of the signal, i.e., either $M_X$ or $M_Y$ but not both. Since the total signal on the xy-plane is $M_{xy}=M_x+iM_y$, the phase of the second 90° pulse determines whether the real or the imaginary part of the signal is preserved for imaging later in the sequence. Assuming that a second 90° RF pulse along the same axis as the first preserves the real part, then one can write this portion of the magnetization as $$M_X = \frac{M_X + iM_Y}{2} + \frac{M_X - iM_Y}{2} = \frac{1}{2}(M_{XY} + M_{XY}^*)$$

In other words, the real part of the signal can be described as the sum of the total signal plus its complex conjugate. Similarly, if a second experiment is carried out with the second RF pulse applied with a 90° phase relative to the first RF pulse then the imaginary part of the signal is preserved. This can be written as $$M_Y = i \cdot \frac{M_X + iM_Y}{2} - i \cdot \frac{M_X - iM_Y}{2} = \frac{i}{2}(M_{XY} - M_{XY}^*)$$

The imaginary part of the signal can be written as the difference between the total signal and its complex conjugate. By acquiring $M_X$ and $M_Y$ by means of two measurements, the individual $M_{XY}$ and $M_{XY}^*$, which correspond to the STE and STAE, respectively, can be decoupled from one another without the limits of the above equations. FID suppression can be accomplished as well by acquiring data from a third experiment with the phase of the third 90° pulse modified accordingly.

Rotating Wheel Method

In phase-labeled imaging, phase-labeled components of magnetization decay or lose coherence via several processes that are conventionally characterized by time constants $T_1$, $T_2$, and $T_2^*$. Many of the limitations imposed by these decay processes can be overcome as follows, with a rotating wheel method illustrated in FIG. 13. Such a method permits voxel motion to be tracked at a series of times. For a magnetization that, at time $t_1$, is phase-labeled so that $$M_z = \{m(r)e^{i[f(r)-\phi]} - m(r)e^{-i[f(r)-\phi]}\}/(2i), \quad M_{xy} = \{m(r)e^{i[f(r)-\phi]} + m(r)e^{-i[f(r)-\phi]}\}/2$$

and the initial coherence in $M_{xy}$ is retained for a substantial period of time, both $M_z$ and $M_{xy}$ are used for data acquisition. Data is acquired at a series of time points $t_n$ after the initial phase labeling using a series of RF pulses and readout schemes that satisfies three conditions: (a) at each time point $t_n$, readout-induced phase dispersion in $M_{xy}$ is refocused with gradient pulses before the next time point; (b) at some time points $t_n$, a portion of $M_z$ is tipped onto the transverse plane to replenish magnetization losses due to decay in $M_{xy}$ due to various relaxation processes, while a portion of the refocused $M_{xy}$ is tipped into the longitudinal axis for storage; and (c) at least some adjacent RF pulses produce a nearly 180° flip, so that phase dispersion due to field inhomogeneities in $B_0$ are compensated, and the decay of the transverse component $M_{xy}$ follows approximately the $1/T_2$ rate. When these three conditions are satisfied, the phase-labeled transverse magnetization acquired at the time points decays at roughly the rate of $1/T_2$, while it is continuously or intermittently replenished by the labeled terms in the longitudinal magnetization that decay at the slower $1/T_1$ rate in most biological samples. An advantage of this method is that the labeled terms in $M_{xy}$ are used to improve SNR, while the available acquisition time is increased by continuously or intermittently storing part of $M_{xy}$ on the longitudinal axis and replenishing $M_{xy}$ with a portion of the phase-labeled magnetization $M_z$. By adjusting the RF pulse flip angles, the amount of $M_z$ tipped into the transverse plane at each time point is controlled, and therefore the total time available for data acquisition is controlled. Generally, there exists a tradeoff between the data acquisition time and the SNR at each time point, and one can choose a suitable balance between the two by adjusting the RF pulses, as well as how frequently $M_z$ is tipped in the transverse plane to replenish $M_{xy}$.

In one example of phase labeling, the magnetizations of all voxels in a region of interest form spokes of a wheel in a plane perpendicular to the xy plane, after phase labeling as shown in FIG. 12. The axis of the wheel is in the xy plane at an angle $\phi+\pi/2$ from the x axis. At time $t_2$, a gradient-balanced RF pulse combination of flip angle $\alpha$ is applied along this direction (the direction perpendicular to the direction of the last 90° pulse in the phase labeling). This pulse turns the wheel around its axis by angle $\alpha$ as shown in FIG. 12, so that the longitudinal and transverse magnetizations are $$M_z = m(r')\{e^{i[f(r')-\phi-\pi/2-\alpha]} + m(r)e^{-i[f(r')-\phi-\pi/2-\alpha]}\}/2,$$

$$M_{xy} = m(r')\{e^{i[f(r')-\phi-\alpha]} + m(r)^* e^{-i[f(r')-\phi-\alpha]}\}/2,$$

wherein $r'=r(t_1)$. One or more of the readout methods described above can be used to acquire $M_{xy}$ and isolate the phase-label function $f(R')$. All gradients used during the readout period are rewound so that $M_{xy}$ is restored to the form above.

At time $t_3$, a gradient-balanced $\alpha$ RF pulse is applied along the direction $\phi+\pi/2$. The magnetizations are then:

$$M_z = m(r')\{e^{i[f(r')-\phi-\pi/2-2\alpha]} + m(r)^* e^{-i[f(r')-\phi-\pi/2-2\alpha]}\}/2,$$

$$M_{xy} = m(r')\{e^{i[f(r')-\phi-2\alpha]} + m(r)^* e^{-i[f(r'))-\phi-2\alpha]}\}/2.$$

The readout and gradient rewinding process done at $t_2$ is performed again to acquire $M_{xy}$.

This process can be repeated for the series of time points: At each time $t_n$, an $\alpha$ RF pulse tips part of the longitudinal magnetization $M_z$ onto the xy-plane and restores part of the $M_{xy}$ along the z-axis. Mathematically, this is reflected as adding and subtracting $\alpha$ to the phases of the two terms in $M_z$ and $M_{xy}$. FIG. 13 is a schematic diagram representation of such a pulse sequence, where the readout after each $\alpha$ pulse is a gradient-recalled-echo readout. On average, the magnetization vector of a voxel spends equal times in the transverse plane and along the main field. Thus, the coherence of the magnetization decays at roughly half the rate of its relaxation in the transverse plane (assuming the relaxation rate along the longitudinal direction is much lower). Because several consecutive $\alpha$ pulses approach a 180° RF pulse, any phase dispersion of the transverse magnetization due to $B_0$ inhomogeneity is refocused after several $\alpha$ pulses.

FIG. 13 illustrates one embodiment of the rotating-wheel acquisition method for mapping an x-component of the displacement at multiple time points. The phase-labeling segment consists of a 90° RF pulse followed by a gradient pulse, and then another 90° flip along the x-axis. This creates a spin wheel, with $M_z = (e^{ikz} - e^{-ikz}) M_0/(2i)$, $M_{xy} = (e^{ikx} + e^{-ikx}) M_0/2$. A fully balanced readout gradient is preferably applied to sample both terms of the transverse magnetization $M_{xy}$ simultaneously, as represented by the two echoes above the readout period. The magnetization is returned to the above spin-wheel form after the balanced readout. Then, at time $t_1+\Delta t$, an RF pulse of $\alpha$ flip angle is preferably applied around the y-axis, and the balanced readout is repeated. At time $t_1+2\Delta t$, this process is repeated again. During each readout period, the gradient waveforms are fully balanced (net time integral of the gradient waveforms is zero), so as not to add additional phase to the magnetization. This process is repeated for a series of time point $t_1+n\Delta t$.

Each RF pulse is in this sequence, including the 90° pulses in the phase-labeling section, are fully balanced so as not to leave residual phase dispersion on the magnetization vectors, regardless of the initial orientation of the magnetization vector. A fully balanced slice-selective RF pulse 1302 in the form of a sinc function is illustrated in FIG. 13. The gradient area G under the slice-select gradient pulse is balanced by two gradient pulses of opposite sign and half the area (G/2), one applied immediately before the slice-select gradient pulse, the other immediately after the slice-select gradient pulse.

In biological samples, usually $T_1 \gg T_2$, so the MR signal in this method lasts approximately twice $T_2$, during which the desired function $f(r(t_n))-f(r(t_1))$ is repeatedly mapped to form a history of motion.

The RF pulses at the time points $t_n$ need not have the same flip angle. As long as the flip angle for each pulse is known, the phase offsets brought about by the RF pulse to the terms in $M_z$ and $M_{xy}$ are known and preferably compensated for during image reconstruction. In cases where the flip angle is not exactly uniform in the region of interest, for example, with slice profile imperfections in slice-selective RF pulses, this flexibility allows several RF pulses to be used in one direction of spin rotation, and then an equal number of pulses in the other direction to compensate for the imperfections. In the pulse sequence of FIG. 13, this is implemented by replacing the series of α pulses with a series of +α and −α pulses, e.g., (+α, +α, +α, +α, −α, −α, −α, −α, +α, +α, +α, +α, −α, −α, −α, −α, . . . ).

This analysis leads to other embodiments in which the RF pulses for the time series alternate between 180° −α and −(180° −α), α being a small angle (e.g., 30°). Since each RF flip is about 180°, it refocuses most of the phase dispersions in $M_{xy}$ due to $B_0$ inhomogeneities. In the meantime, with each RF pulse a 1-cos(α) portion of the longitudinal magnetization $M_z$ is preferably brought into the transverse plane to replenish $M_{xy}$, while a 1-cos(α) portion of the transverse magnetization $M_{xy}$ is brought back to the z axis for storage. By reducing the angle α, the sustainable acquisition time approaches $T_1$, while SNR at each time point is reduced. Raising α has the opposite effect.

In other embodiments, one can replace the α-pulse train in FIG. 13 with a repeating segment consisting of an even number of alternating 180° and −180° pulses followed by a small tip angle α pulse, i.e., (180, −180, 180, −180, α, 180, −180, 180, −180, α, . . . ). In each segment, the series of 180 pulses repeatedly refocus as the transverse magnetization $M_{xy}$ for readout, and then the α pulse tips a portion of the longitudinal magnetization into the transverse plane to replenish $M_{xy}$ in preparation for data acquisition in the next segment.

Further embodiments include reading the transverse phase-encoded magnetization with a train of 180-degree pulses, right after the phase label has been applied. The signal sampled during the series of 180-degree pulses can be used to form images, which posses phase-labeled information at different time points. The length of this readout period will be limited by $T_2$ relaxation. Once the transverse magnetization has decayed and is no longer useful for creating images, it is crushed by gradient pulses. Following this, a 90-degree pulse can be utilized to bring the longitudinal magnetization onto the transverse plane. This part of the magnetization has experienced $T_1$ relaxation ($T_1$ relaxation $(T_1 \gg T_2)$ and, as such, has not decayed significantly. Imaging can now resume with a train of 180-degree pulses as mentioned above, to collect data from more time points.

There are many other possible embodiments of this general method in using a combination of other RF pulse series and readout schemes. If the RF pulses are slice selective, then the slice selective gradient needs to be fully balanced to avoid unwanted phase dispersion in the through-slice direction. FIG. 13 illustrates such a fully balanced slice selective pulse.

This method is called the rotating-wheel method because the magnetization vectors form a vertical wheel in the spin space after phase labeling, and the wheel rotates around its axis during data acquisition (See FIG. 12).

A cycling between imaging and storing magnetization along the z-axis can be maintained by applying a series of gradient-balanced 90° RF pulses. In this series, the phase of the 90° RF pulses can be changed by 180° after every four such pulses. By doing so, for every eight RF pulses, any deviations from a true 90° rotation are compensated for. In addition, both halves of the magnetization spend equal time along the longitudinal axis and the transverse plane. As a result they decay according to the same decay-rate, which is approximately two times $T_2$. Field inhomogeneity is compensated for by the RF-train phase cycling scheme since the spins spend equal time along both positive and negative directions on the XY-plane. Since for half the time the magnetization is protected from $T_2$ decay by storage along the Z-axis, the decay rate due to spin-spin relaxation is $2T_2$. This is true only when $T_1 \gg T_2$, which is the case for non-contrast-enhanced specimens. For the portion of the magnetization being imaged, either one or both of the STE and STAE can be sampled as described previously. Since all RF pulses used are slice-selective, through-plane motion may cause significant signal loss, especially for later acquisition windows. Increasing the slice-thickness of the pulses in the RF pulse series that follows the position-encoding gradient can provide slice tracking in order to avoid undesired signal loss. However, out-of-slice free induction decay (FID) contributions can degrade image quality. In cases of significant through-slice motion, this problem can be solved by placing out-of-slice saturation pulses immediately before the position-encoding segment.

The acquisition methods can be adapted for mapping phase labels at a series of time points to track motion. At each time point after the initial phase labeling, a fraction of the longitudinal magnetization is tipped onto the transverse plane, and data corresponding to the resulting transverse magnetization is acquired as described above. After data acquisition, the remaining transverse magnetization can be destroyed with gradient spoiler pulses, and this procedure repeated until the phase-labeled longitudinal magnetization is exhausted. To ensure that only a fraction of the phase-labeled longitudinal magnetization $M_z$ is used each time, the tip angle of the decoding RF-gradient waveform is preferably much less than 90°, e.g., 30°.

Free Induction Decay Suppression

FIG. 14 illustrates a DENSE measurement method. Referring to FIG. 14, during a time period TM between a second 90 degree pulse 1402 and a third 90 degree pulse 1404, the magnetization relaxes due to energy dissipation onto the lattice according to $T_1$ to produce a contribution $M_{FID}$ to the z-component of the magnetization. In the presence of an axial magnetic field $B_0$ that establishes an equilibrium +z-directed magnetization $M_z$ (in the absence of RF pulses), a magnetization of magnitude $M_{initial} < M_z$ decays to form a z-component of magnetization M(t), wherein $M(t) = M_z + (M_{initial} - M_z) \exp(-t/T_1)$. After a first 90 degree pulse 1406, the unlabeled transverse magnetization has a zero z-component so that $M_{FID} = M_z[1 - \exp(-\tau_1/T_1)]$ at a time $\tau_1$, wherein $T_1$ is a longitudinal magnetization relaxation time. A 180 degree pulse 1408 flips $M_{FID}$ to be directed along the −z axis, i.e., $M_{FID} = -M_{FID}$. This flipped magnetization relaxes to produce a z-component of magnetization $M(\tau_2)$ at a selected time $\tau_2$ and has a magnitude that can be determined by assigning $M_{initial}$ the value of $M_{FID}$ so that $M(\tau_2) = M_z + [-M_z(1 - \exp(-\tau_1/T_1)) - M_z] \exp(-\tau_2/T_1)$. The duration $\tau_1$ and $\tau_2$ can be selected so that at time $\tau_2$, $M(\tau_2) = 0$ by selecting $\tau_2=T_1 \ln[2/(1+\exp(-T_M/T_1)]$. As a representative example, for a mixing time $T_M=300$ ms and a longitudinal relaxation time $T_1=300$ ms, $\tau_1=262.2$ ms and $\tau_2=138.8$ ms.

Selection of $\tau_1$ and $\tau_2$ for FID suppression depends on the longitudinal relaxation time $T_1$ and because $T_1$ is generally material dependent. For example, for myocardial tissue $T_1$ is approximately 850 ms while for fat tissue, $T_1$ is approximately 200 ms. However, FID associated with two time constants can be suppressed by providing an additional 180 degree pulse and corresponding time intervals.

Reduction of Phase Errors by Interleaved Data Acquisition

Phase-labeled terms acquired during readout contain the phase-label function as well as other additional phase contributions from eddy currents, $B_0$ inhomogeneities, etc. These contributions bring errors into the measurement. One method of removing these phase errors is to acquire two data sets that are phase-labeled with different functions, af(r) and bf(r), where a and b are different constants. These two data sets share the same unknown phase contributions. By subtracting their respective results, we obtain (a−b)[f(r')−f(r)], and the common phase errors are removed. These two data sets can be acquired under the same condition of motion, preferably in an interleaved fashion, to reduce errors from small changes in the position and movement of the object.

Resolving Phase Ambiguities

The phase of an MRI signal is normally expressed in the range of 0 to $2\pi$ radians. When a specified phase-label function exceeds this range, the acquired phase-label distribution contains step-like jumps of $2\pi$ magnitude. This phenomenon is called "phase wrap-around." Phase wrap-around is corrected by first locating the discontinuous boundaries where this jump occurs, and then, for each boundary, the phase of the voxels on one side of the boundary is added or subtracted with an integer multiple of $2\pi$, such that the discontinuity is removed. This procedure is generally effective. In some specimens, a bulk motion of an isolated region needs to be measured in relation to other regions and phase differences between these regions are ambiguous. In diagnostic imaging, the purpose of motion tracking is usually to characterize the internal movements of a contiguous area, where phase unwrapping is sufficient to resolve the ambiguity. In certain applications, measurements of local tissue deformation are needed, such as the strain in the myocardium. For these applications, it is not necessary to unwrap the phase for the entire region of interest as a whole, but rather it is sufficient to phase-unwrap each small area encompassing a group of neighboring voxels, and obtain the local deformation in this area.

Strain Data Display

In certain applications of MRI motion tracking, it is advantageous to quantify the deformation of a region by computing material strain. An example is strain mapping in the myocardium. In a two-dimensional (2D) plane, such as a 2D image through the long axis of the left ventricle, strain tensor maps can be calculated once the in-plane components of displacement vectors are mapped with one or more of the methods described in the previous sections. The strain tensor at each voxel is represented by the strain values (negative for compression and positive for stretching) along two orthogonal directions, called principal axes of strain. Both the strain values and the principal axes contain useful information in many cases. The strain values can be display using short, thick line segments of uniform length to represent the principal axes at each voxel, while the a color or a grayscale intensity of the line segments represent the strain values. The strain data can be presented in two strain images, each containing strain values of a particular sign, so that one map presents the axes and strain values for compression, while the other presents the axes and strain values for stretching. The color or grayscale intensity in each map represents the absolute value of the positive or negative strain. If a voxel has the same sign of strain for both principal axes, then in one map, two orthogonal line segments appear in its position, while in the other map the line segments are absent.

Alternatively, the strain data can be separated into two maps containing the higher and lower strain values, respectively. Then, each voxel in a map contains one line segment, whose color or grayscale intensity represents the corresponding strain value. Since each map may contain both positive and negative strain values, the color scale or gray intensity scale may need to represent a range of values from negative to positive, and a mixture of color and gray-intensity scale can be used for this purpose.

Strain data can also be displayed in a single image by providing each voxel with orthogonal line segments of uniform length to represent the principal axes of strain. The color or grayscale intensity of each line segment represents the corresponding strain value. A mixture of color scale and gray intensity scale can be used to cover a range of values including both negative and positive numbers.

Example embodiments of the invention are described above. It will be appreciated that these embodiments can be modified in arrangement and detail without departing from the scope of the invention.

We claim:

1. A magnetic resonance imaging method, comprising:
applying a first excitation radio-frequency (RF) pulse along a first excitation axis to produce a first transverse magnetization;
applying a first position encoding phase label to the first transverse magnetization;
storing a component of the position encoded first transverse magnetization as a first stored longitudinal magnetization by applying a first storing RF pulse along a first storing axis;
allowing a first mixing time interval of duration $T_M$ to elapse;
after the first mixing time has elapsed, producing a transverse magnetization based on the first stored longitudinal magnetization;
decoding the transverse magnetization produced after the first mixing time;
generating a first image signal based on the decoded transverse magnetization produced after the first mixing time;
applying a second excitation RF pulse along a second excitation axis to produce a second transverse magnetization;
applying a second position encoding phase label to the second transverse magnetization;
storing a component of the position encoded second transverse magnetization as a second stored longitudinal magnetization by applying a second storing RF pulse along a second storing axis, wherein a difference between an angle from the first excitation axis to the first storing axis and an angle from the second excitation axis to the second storing axis is not an integer multiple of 180 degrees;
allowing a second mixing time of duration $T_M$ to elapse;
after the second mixing time has elapsed, producing a transverse magnetization based on the second stored longitudinal magnetization;

decoding the transverse magnetization produced after the second mixing time;

generating a second image signal based on the decoded transverse magnetization produced after the second mixing time; and combining the first image signal and the second image signal to reduce a contribution associated with a complex conjugate of a phase-labeled magnetization to obtain an artifact-reduced image of a specimen.

2. The method of claim 1, further comprising estimating specimen motion based on the combined first image signal and second image signal.

3. The method of claim 2, wherein the first excitation axis and the first storing axis are orthogonal.

4. The method of claim 2, further comprising:

dividing the mixing time intervals of duration $T_M$ into a first interval of duration $t_1$ and a second interval of duration $t_2$, where the first and second intervals are selected based on at least one longitudinal decay time $T_1$; and applying a 180° radio-frequency (RF) pulse to the specimen after the time interval $t_1$ during acquisition of both the first image signal and the second image signal to reduce contributions associated with free induction decay.

5. The method of claim 4, wherein time points within the mixing time intervals divide the mixing time intervals into a first interval of duration $t_1$ and a second interval of duration $t_2$ such that $t_2=\ln [2/(1+\exp(-T_M/T_1))]$, wherein $T_1$ is a longitudinal decay time and $T_M=t_1+t_2$.

6. The method of claim 2, further comprising applying RF pulses to the specimen at time points within the mixing time intervals, wherein the time points are selected to reduce a contribution to the image signals from free induction decay.

7. The method of claim 1, wherein the first and second position encoding phase labels are applied along a selected displacement direction.

8. The method of claim 7, further comprising estimating specimen motion based on the combined first image signal and second image signal.

9. The method of claim 8, wherein the first excitation axis and the first storing axis are orthogonal.

10. The method of claim 8, further comprising:

dividing the mixing time intervals of duration $T_M$ into a first interval of duration $t_1$ and a second interval of duration $t_2$, wherein the first and second intervals are selected based on at least one longitudinal decay time $T_1$; and applying a 180° radio-frequency (RF) pulse to the specimen after the time interval $t_1$ during acquisition of both the first image signal and the second image signal to reduce contributions associated with free induction decay.

11. The method of claim 8, wherein time points within the mixing time intervals divide the mixing time intervals into a first interval of duration $t_1$ and a second interval of duration $t_2$ such that $t_2=\ln [2/(1+\exp(-T_M/T_1))]$, wherein $T_1$ is a longitudinal decay time and $T_M=t_1+t_2$.

12. The method of claim 8, further comprising applying RF pulses to the specimen at time points within the mixing time intervals, wherein the time points are selected to reduce a contribution to the image signals from free induction decay.

13. A magnetic resonance imaging method, comprising:

applying a first excitation radio-frequency (RF) pulse along a first excitation axis to produce a first transverse magnetization;

applying a first position encoding phase label to the first transverse magnetization;

storing a component of the position encoded first transverse magnetization as a first stored longitudinal magnetization by applying a first storing RF pulse along a first storing axis;

allowing a first mixing time interval of duration $T_M$ to elapse;

after the first mixing time has elapsed, producing a transverse magnetization based on the first stored longitudinal magnetization;

decoding the transverse magnetization produced after the first mixing time;

generating a first image signal based on the decoded transverse magnetization produced after the first mixing time;

applying a second excitation RF pulse along a second excitation axis to produce a second transverse magnetization;

applying a second position encoding phase label to the second transverse magnetization;

storing a component of the position encoded second transverse magnetization as a second stored longitudinal magnetization by applying a second storing RF pulse along a second storing axis;

allowing a second mixing time of duration $T_M$ to elapse;

after the second mixing time has elapsed, producing a transverse magnetization based on the second stored longitudinal magnetization;

decoding the transverse magnetization produced after the second mixing time;

generating a second image signal based on the decoded transverse magnetization produced after the second mixing time;

applying a third excitation RF pulse along a third excitation axis to produce a third transverse magnetization;

applying a third position encoding phase label to the third transverse magnetization;

storing a component of the position encoded third transverse magnetization as a third stored longitudinal magnetization by applying a third storing RF pulse along a third storing axis, wherein an angle from the first excitation axis to the first storing axis, an angle from the second excitation axis to the second storing axis, and an angle from the third excitation axis to the third storing axis are different;

allowing a third mixing time interval of duration $T_M$ to elapse;

after the third mixing time has elapsed, producing a transverse magnetization based on the third stored longitudinal magnetization;

decoding the transverse magnetization produced after the third mixing time;

generating a third image signal based on the decoded transverse magnetization produced after the third mixing time; and combining the first, second, and third image signals to reduce either a contribution associated with a complex conjugate of a phase-labeled magnetization or free induction decay, or both to obtain an artifact-reduced image of a specimen.

14. The method of claim 13, further comprising estimating specimen motion based on the combined first, second, and third image signals.

15. The method of claim 14, further comprising:

dividing the mixing time intervals into a first interval of duration $t_1$ and a second interval of duration $t_2$, wherein the first and second intervals are selected based on at least one longitudinal decay time $T_1$; and applying a 180° radio-frequency (RF) pulse to the specimen after the time interval $t_1$ during acquisition of the image signals to reduce contributions associated with free induction decay.

16. The method of claim 15, wherein the first interval of duration $t_1$ and the second interval of duration $t_2$ are selected such that $t_2 = T_1 \ln[2/(1+\exp(-T_M/T_1))]$, and $T_M = t_1 + t_2$.

17. The method of claim 14, further comprising applying radio-frequency (RF) pulses to the specimen at time points within the mixing time intervals, wherein the time points are selected to reduce contributions to the image signals from free induction decay.

18. The method of claim 13, wherein the first, second, and third position encoding phase labels are applied along a selected displacement direction.

19. The method of claim 18, further comprising estimating specimen motion based on the combined first, second, and third image signals.

20. The method of claim 19, further comprising:
dividing the mixing time intervals into a first interval of duration $t_1$ and a second interval of duration $t_2$, wherein the first and second intervals are selected based on at least one longitudinal decay time $T_1$; and applying a 180° radio-frequency (RF) pulse to the specimen after the time interval $t_1$ during acquisition of the image signals to reduce contributions associated with free induction decay.

21. The method of claim 20, wherein the first interval of duration $t_1$ and the second interval of duration $t_2$ are selected such that $t_2 = T_1 \ln[2/(1+\exp(-T_M/T_1))]$, and $T_M = t_1 + t_2$.

22. The method of claim 19, further comprising applying radio-frequency (RF) pulses to the specimen at time points within the mixing time intervals, wherein the time points are selected to reduce contributions to the image signals from free induction decay.

23. A magnetic resonance imaging method, comprising:
applying an excitation radio-frequency (RF) pulse along an excitation axis to produce a transverse magnetization;

applying a position encoding phase label to the transverse magnetization;

storing a component of the position encoded transverse magnetization as a stored longitudinal magnetization by applying a storing RF pulse along a storing axis;

allowing a mixing time interval of duration $T_M$ to elapse;

applying an RF pulse at a time point within the mixing time interval, wherein the time point is selected to reduce a signal contribution from free induction decay;

after the first mixing time has elapsed, producing a transverse magnetization based on the stored longitudinal magnetization;

decoding the transverse magnetization produced after the mixing time;

generating an image signal of a specimen and producing an associated image of the specimen based on the decoded transverse magnetization produced after the mixing time.

24. The method of claim 23, further comprising estimating specimen motion based on the generated image signal.

25. The method of claim 24, further comprising:
dividing the mixing time interval into a first interval of duration $t_1$ and a second interval of duration $t_2$, wherein the first and second intervals are selected based on at least one longitudinal decay time $T_1$; and applying a 180° radio-frequency (RF) pulse to the specimen after the time interval $t_1$.

26. The method of claim 25, wherein the time point within the mixing time interval divides the mixing time interval into a first interval of duration $t_1$ and a second interval of duration $t_2$ such that $t_2 = \ln[2/(1+\exp(-T_M/T_1))]$, wherein $T_1$ is a longitudinal decay time and $T_M = t_1 + t_2$.

27. The method of claim 23, wherein the position encoding phase label is applied along a selected displacement direction.

28. The method of claim 27, further comprising estimating specimen motion based on the generated image signal.

29. The method of claim 28, further comprising:
dividing the mixing time interval into a first interval of duration $t_1$ and a second interval of duration $t_2$, wherein the first and second intervals are selected based on at least one longitudinal decay time $T_1$; and applying a 180° radio-frequency (RF) pulse to the specimen after the time interval $t_1$.

30. The method of claim 29, wherein the time point within the mixing time interval divides the mixing time interval into a first interval of duration $t_1$ and a second interval of duration $t_2$ such that $t_2 = \ln[2/(1+\exp(-T_M/T_1))]$, wherein $T_1$ is a longitudinal decay time and $T_M = t_1 + t_2$.

* * * * *